US011951210B2

(12) United States Patent
Razavi et al.

(10) Patent No.: US 11,951,210 B2
(45) Date of Patent: Apr. 9, 2024

(54) METHODS FOR MAKING GIANT VESICLES AND THEIR USE

(71) Applicant: THE JOHNS HOPKINS UNIVERSITY, Baltimore, MD (US)

(72) Inventors: Shiva Razavi, Baltimore, MD (US); Takanari Inoue, Lutherville-Timonium, MD (US); Tianzhi Luo, Anhui (CN); Douglas Robinson, Lutherville-Timonium, MD (US)

(73) Assignee: THE JOHNS HOPKINS UNIVERSTY, Baltimore, MD (US)

( * ) Notice: Subject to any disclaimer, the term of this patent is extended or adjusted under 35 U.S.C. 154(b) by 0 days.

(21) Appl. No.: 16/772,518

(22) PCT Filed: Dec. 12, 2018

(86) PCT No.: PCT/US2018/065237
§ 371 (c)(1),
(2) Date: Jun. 12, 2020

(87) PCT Pub. No.: WO2019/118621
PCT Pub. Date: Jun. 20, 2019

(65) Prior Publication Data
US 2021/0145746 A1 May 20, 2021

Related U.S. Application Data

(60) Provisional application No. 62/597,631, filed on Dec. 12, 2017.

(51) Int. Cl.
*A61K 9/127* (2006.01)
(52) U.S. Cl.
CPC .......... *A61K 9/1271* (2013.01); *A61K 9/1277* (2013.01)

(58) Field of Classification Search
CPC ..... A61K 9/1271; A61K 9/127; A61K 9/1277
See application file for complete search history.

(56) References Cited

U.S. PATENT DOCUMENTS

2013/0028963 A1* 1/2013 Fletcher ............... A61K 9/1271
424/94.1

FOREIGN PATENT DOCUMENTS

WO 2015/014965 A1 2/2015
WO WO 2015/014965 2/2015

OTHER PUBLICATIONS

Alexander Moscho, Owe Orwar, Daniel T. Chiu, Biren P. Modi, and Richard N. Zare. "Rapid preparation of giant unilamellar vesicles." Proceedings of the National Academy of Sciences, vol. 93, Oct. 1996, pp. 11443-11447. (Year: 1996).*

(Continued)

*Primary Examiner* — Isaac Shomer
(74) *Attorney, Agent, or Firm* — Casimir Jones, SC; Jeffrey W. Childers

(57) ABSTRACT

This application is directed to methods which allow for encapsulation of an array of biological materials under physiological conditions that are relevant given a biological context and the compositions made using those methods. These reconstituted biological materials encompass: a) purified proteins that can bind to the lipid membranes inside and outside of vesicles based on the electrostatic charge; b) purified cytosolic proteins that position themselves in the lumen of the vesicles, c) mammalian cell extracts with an array of cytosolic protein content, among other contents and d) small biological molecules such as DNA and RNA as well as fluorescent dyes/probes. These vesicles can be used to simulate cells in drug discovery methods as well as useful in administering drugs and other compositions to cells in vitro and in vivo.

5 Claims, 11 Drawing Sheets

(56) References Cited

OTHER PUBLICATIONS

Kevin Carvalho, Laurence Ramos, Christian Roy, and Catherine Picart. "Giant Unilamellar Vesicles Containing Phosphatidylinositol(4,5)bisphosphate: Characterization and Functionality." Biophysical Journal, vol. 95, Nov. 2008, pp. 4348-4360. (Year: 2008).*
Urszula Golebiewska, Marian Nyako, William Woturski, Irina Zaitseva, and Stuart McLaughlin. "Diffusion Coefficient of Fluorescent Phosphatidylinositol 4,5-bisphosphate in the Plasma Membrane of Cells." Molecular Biology of the Cell, vol. 19, Apr. 2008, pp. 1663-1669. (Year: 2008).*
Catherine B. Carbone et al. "In vitro reconstitution of T cell receptor-mediated segregation of the CD45 phosphatase." Proceedings of the National Academy of Sciences, Published online Oct. 17, 2017, pp. E9338-E9345. (Year: 2017).*
Youngdae Yoon, Xiuqi Zhang, and Wonhwa Cho. "Phosphatidylinositol 4,5-Bisphosphate (PtdIns(4,5)P2) Specifically Induces Membrane Penetration and Deformation by Bin/Amphiphysin/Rvs (BAR) Domains." The Journal of Biological Chemistry, vol. 287, No. 41, 2012, pp. 34078-34090. (Year: 2012).*
Alok Gambhir et al. "Electrostatic Sequestration of PIP2 on Phospholipid Membranes by Basic/Aromatic Regions of Proteins." Biophysical Journal, vol. 86, Apr. 2004, pp. 2188-2207. (Year: 2004).*
Xiaoying Chen, Jennica L. Zaro, Wei-Chiang Shen. "Fusion protein linkers: Property, design and functionality." Advanced Drug Delivery Reviews, vol. 65 (2013), pp. 1357-1369. (Year: 2013).*
Avanti Lipids. https://avantilipids.com/product/790404 accessed Nov. 21, 2023, pp. 1-3. (Year: 2023).*
Bhatia Tripta et al. Prepairing giant unilamellar vesicles (GUVs) of complex lipid mixtures on demand: Mixing small unilamellar fesicles of compositionally heterogeneous mixtures. Biocimica et Biopysica Acta. 2015, 1848(12):pp. 3175-3180, pp. 2-4.
Montes L.-Ruth et al. Electroformation of Giant Unilamellar Vesicles from Native Membranes and Organic Lipid Mixtures for the Study of Lipid Domains under Physiological Ionic-Strength Conditions. Liposomes: Methods and Protocols. 2010; 606:105-114, pp.
International Search Report and Written Opinion for PCT/US2018/065237, dated Apr. 25, 2019, 5 pages.
Bhatia, T., et al., "Preparing giant unilamellar vesicles (GUVs) of complex lipidmixtures on demand: Mixing small unilamellar vesicles of compositionally heterogeneous mixtures" Biochimica et Biophysica Acta 1848 (2015) 3175-3180.
Montes, L., et al., "Electroformation of Giant Unilamellar Vesicles from Native Membranes and Organic Lipid Mixtures for the Study of Lipid Domains under Physiological Ionic-Strength Conditions" (2010) Liposomes: Methods and Protocols, vol. 2: Biological Membrane Models, Methods in Molecular Biology, vol. 606, DOI 10.1007/978-1-60761-447-0_9, pp. 105-114.

* cited by examiner

METHODS FOR MAKING GIANT VESICLES AND THEIR USE

CROSS-REFERENCE TO RELATED APPLICATIONS

This application is a 35 U.S.C. § 371 U.S. national entry of International Application PCT/US2018/065237, having an international filing date of Dec. 12, 2018, which claims the benefit of U.S. Provisional Application No. 62/597,631, filed Dec. 12, 2017, the content of each of the aforementioned applications is herein incorporated by reference in their entirety.

BACKGROUND OF THE INVENTION

Making artificial cells that can recapitulate cells in terms of geometry, lipid composition, and functionality has been a burgeoning challenge in the field of synthetic biology. Such artificial cells or giant vesicles are also of interest as biomimetic devices with potential applications in drug delivery due to their biocompatibility as cell-like entities. Techniques have been developed to fabricate this class of giant vesicles such that they mimic cells in terms of geometry, membrane unilamellarity, and lipid composition. However, encapsulating biological material inside such vesicles in a physiologically relevant environment (in terms of buffer and temperature conditions) has been a challenge. Furthermore, making these vesicles with the goal of membrane permeability with respect to various chemical targets has not been realized before.

SUMMARY OF THE INVENTION

This application is directed to compositions and methods which allow for encapsulation of an array of biological materials (i.e. protein, peptides, dyes, cell extracts, DNA, RNA, dyes, buffers, etc.) under physiological conditions that are relevant in a given biological context. These reconstituted biological materials comprise: a) purified proteins that can bind to the unilamellar lipid membranes inside and outside of vesicles based on the electrostatic charge; b) purified cytosolic proteins that position themselves in the lumen of the vesicles, and c) mammalian cell extracts with an array of cytosolic protein content, among other contents. Moreover, the inventive compositions and methods described herein allow for on-demand modification of the localization of the protein/peptide components from the lumen to the membrane in response to administration of the chemical of choice, rapamycin, which permeates across the membrane of the vesicles fabricated.

As such, in accordance with an embodiment, the present invention provides methods for making giant unilamellar vesicles (GUV) comprising the steps of a) solubilizing at least a first and second lipid mixture with a suitable non-polar solvent, wherein the first lipid mixture contains lipids for the inner lipid layer of the vesicle and the second lipid mixture contains lipids for the outer lipid layer of the vesicle; b) drying the mixtures of a) under vacuum for a sufficient time; c) dissolving the dried mixtures of b) in a long chain alkane non-polar solvent; d) heating the solutions of c) in a closed container at a temperature between 60-80° C. for about 2-5 hours; e) assembling a vesicle outer leaflet by layering the solubilized outer lipid mixture from d) on the surface of a disaccharide solution for at least 3 to 10 minutes to allow a monolayer to form on the surface of the disaccharide solution; f) dissolving the solubilized inner lipid mixture from d) in an oil solution at a concentration of about 0.5 to 2 mg/ml; g) combining the solution of f) with a solution of luminal content of interest and agitate the combination with sufficient force to create a homogenous emulsion; h) add a sufficient volume of the emulsion of g) to the surface of the disaccharide solution of e); i) subject the combination of h) to centrifugation at about 2000-3000×g for about 5-10 minutes to assemble the completed vesicles; and j) remove the completed vesicles from the bottom of the container.

In accordance with an embodiment, the present invention provides giant unilamellar vesicles (GUV) comprising a microparticle having a unilamellar lipid bilayer.

In some embodiments the present invention provides the use of GUV for modeling cellular structures and functions.

In some embodiments the present invention provides the use of GUV for delivery of therapeutic agents and treatment of disease, both in vitro and in vivo.

BRIEF DESCRIPTION OF THE DRAWINGS

In FIGS. 5A, 5C and 5D, normalized fluorescence intensities from lines scans across the representative GUVs are shown, as localizations were uniform for each of these GUV populations. In 5B) the mean normalized fluorescence intensities of line scans across 18 GUV for each condition (+/−GTP) are presented and error bars (thin lines above and below middle line) represent standard deviation. Proteins were used at 2 μM, $MgCl_2$ was present at 2.5 mM in all FtsZ containing reactions and GTP was used at 2 mM. Scale bars 5 μm.

DETAILED DESCRIPTION OF THE INVENTION

Figure 1:
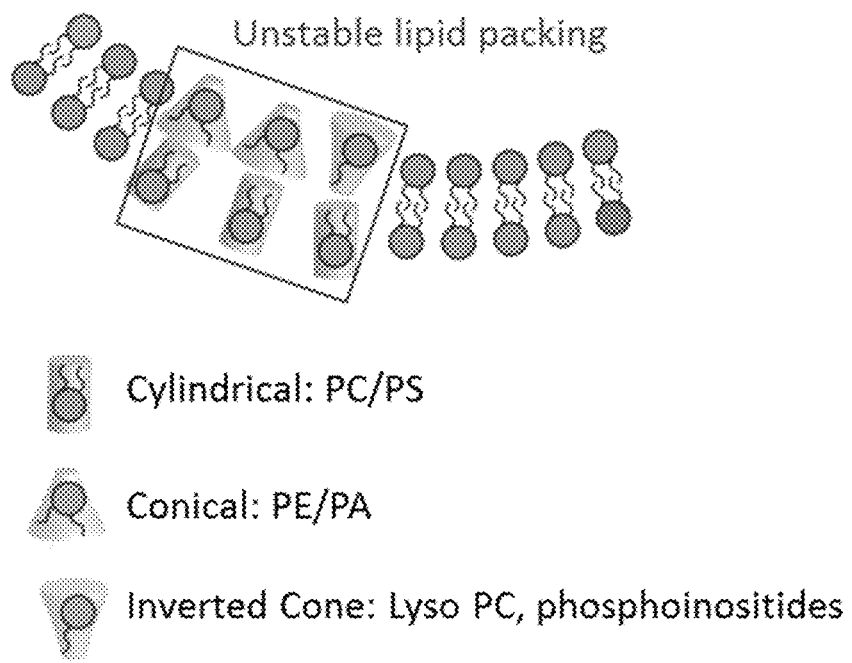
FIG. 1. Description of various lipid shapes and the effect of these geometrical differences on the lipid bilayer packing and stability.

As such, in accordance with an embodiment, the present invention provides methods for making GUV comprising the steps of a) solubilizing at least a first and second lipid mixture with a suitable non-polar solvent, wherein the first lipid mixture contains lipids for the inner lipid layer of the vesicle and the second lipid mixture contains lipids for the outer lipid layer of the vesicle; b) drying the mixtures of a) under vacuum for a sufficient time; c) dissolving the dried mixtures of b) in a long chain alkane non-polar solvent; d) heating the solutions of c) in a closed container at a temperature between 60-80 C for about 2-5 hours; e) assembling a vesicle outer leaflet by layering the solubilized outer lipid mixture from d) on the surface of a disaccharide solution for at least 3 to 10 minutes to allow a monolayer to form on the surface of the disaccharide solution; 0 dissolving the solubilized inner lipid mixture from d) in an oil solution at a concentration of about 0.5 to 2 mg/ml; g) combining the solution of f) with a solution of luminal content of interest and agitate the combination with sufficient force to create a homogenous emulsion; h) add a sufficient volume of the emulsion of g) to the surface of the disaccharide solution of e); i) subject the combination of h) to centrifugation at about 2000-3000×g for about 5-10 minutes to assemble the completed vesicles; and j) remove the completed vesicles from the bottom of the container.

In some embodiments the suitable non-polar solvent can include, but is not limited to methanol, ethanol, chloroform, methylene chloride, carbon tetrachloride, acetonitrile, and hexane, which can also be a mixture of two or more solvents, and, in some cases are mixed with a polar solvent such as water.

In some embodiments the drying time for evaporating the solvent from the lipid mixtures can vary. Examples of suitable drying times includes 4 hours or more, 6 hours or more, 8 hours or more, 10 hours or more and 12 hours or more as needed.

In some embodiments, the long chain alkane non-polar solvent used to redissolve the dried lipid mixtures includes alkane solvents of greater than 10 carbons in length, such as, for example, dodecane, hexadecane, and silicon oil and the like.

In some embodiments, examples of the disaccharide used in the assembly of a vesicle outer leaflet include, but are not limited to, sucrose, lactose, and maltose as well inorganic buffers within such those containing phosphate, Tris, or HEPES within the 7.0 to 8.0 pH range.

In some embodiments, the oil solution used to solubilize the inner lipid mixture can be mineral oil, paraffin oil, silicon oil, hexadecane and the like.

It will be understood that the GUV made using the methods of the present invention comprise microparticulate structures having a unilamellar lipid bilayer.

Therefore, in accordance with an embodiment, the present invention provides giant unilamellar vesicles (GUV) comprising a microparticle having a unilamellar lipid bilayer.

As used herein, the term "unilamellar lipid bilayer" means that the created GUV microparticles comprise a single lipid bilayer comprising an inner "leaflet" or lipid layer of a particular composition, and an outer "leaflet" or lipid layer of a particular composition, which can have the same or different composition as the inner layer. The GUV microparticle is defined as hollow spherical particle comprising the unilamellar lipid bilayer.

As used herein, the lipids that comprise the inner and outer lipid layer of the unilamellar lipid bilayer can be any lipids based on the luminal content desired.

In some embodiments, the lipids can comprise the same or different lipid compositions.

In general, depending on the type of membrane that is being mimicked the lipid combinations are selected. Most biologically compatible lipids can be used, such as, for example, phospholipid classes, like phosphatidic acid (PA) and phosphatidylserine (PS); mono, di, and triglycerides, glycoproteins, ceramides, $C_6$-$C_{22}$ saturated and unsaturated fatty acids; sphingosines, sterols, lipopolysaccharides, cardiolipins, and the like. Combinations of one or more lipids from the same of different classes of lipids are also contemplated.

In some embodiments, where encapsulation of biological material within the lumen of a vesicle is of interest and the exact lipid composition is not of concern, use of 100% Egg-PC (phosphatidylcholine extracted from egg) in both inner and outer leaflets is possible. The neutrally charged phosphatidylcholine lipids do not exhibit electrostatic interaction with the luminal content, thus reducing the chance of inner content-lipid interaction. For instance, based on our observations, some neutrally charged proteins can have unspecific affinity for negatively charged lipids (i.e. PS).

In some embodiments, alternatively using positively charged peptide domains such as myristoylated alanine-rich protein kinase C substrate (MARCKS) or C2 domain of the lactadherin (lact-C2) can be used. In some other embodiments, negatively charged lipids such as phosphatidylserine (PS), phosphatidylinositol 4,5-bisphosphate or ($PIP_2$) in the inner leaflet of the vesicles can be used.

It will be understood by those of ordinary skill in the art, that the size of the GUV can vary and can have diameters of about 1 nm to about 1000 μm. More preferably, the GUV of the present invention can have diameters of between about 1 μm to about 100 μm.

It will be understood by those of ordinary skill in the art, that the GUV of the present invention comprise an outer and inner surface defined by the unilamellar lipid bilayer, and which encompasses an internal space or lumen inside the GUV. The content of the lumen of the GUV can vary and typically will comprise at a minimum the solvent or buffer the GUV are placed or created in.

As used herein, the term "luminal content" of the GUV includes, but is not limited to proteins, peptides, peptide fragments, cell lysates, small organic molecules, peptides, oligonucleotides, aptamers, antibodies, and siRNAs antibodies, nucleic acids such as RNA and DNA, and other small molecules, including but not limited to imaging agents and drugs.

In accordance with some embodiments, the methods disclosed herein include methods for the preparation of luminal content used within the vesicles of the present invention. In an embodiment, the luminal content is prepared by obtaining the luminal content of interest, adding the luminal content to a disaccharide solution or a buffered solution containing PBS, Tris or HEPES which acts as an osmotic agent, and then measuring or calculating the osmotic pressure of the resultant solution. Such osmotic pressure measurements are well known in the art, including, but not limited to use of a micro-osmometer. Similarly, methods of calculating the osmotic pressure of a solution of known composition and concentration is similarly known.

The term "polynucleotide," as used herein, includes and/or is synonymous with "nucleic acid," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

The term "polyribonucleotide," as used herein, includes "ribonucleic acid," "oligoribonucleotide," and "ribonucleic acid molecule," and generally means a polymer of RNA which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It may be suitable in some instances, in an embodiment, for the nucleic acids to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

As used herein, the term "RNA" means a molecule comprising at least one ribonucleotide residue. By "ribonucleotide" is meant a nucleotide with a hydroxyl group at the 2' position of a β-D-ribo-furanose moiety. The terms "RNA," "ribonucleotides" and "polyribonucleotide," also include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA, or internally, for example, at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

As used herein, the term "antibody" means a polypeptide comprising a framework region from an immunoglobulin gene or fragments thereof that specifically binds and recognizes an antigen. Use of the term antibody is meant to include whole antibodies, including single-chain whole antibodies such as IgG, IgA, IgM, IgD, etc., antibody fragments such as Fab fragments, and other antigen-binding fragments thereof. The term "antibody" includes bispecific antibodies and multispecific antibodies so long as they exhibit the desired biological activity or function.

As used herein, "recombinant antibody" refers to a recombinant (e.g., genetically engineered) protein comprising a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. The polypeptide of an antibody, or portion thereof, can be a polypeptide of any antibody or any antibody fragment, including any of the antibodies and antibody fragments described herein.

At least one of the imaging agents is a fluorescent dye. The dyes may be emitters in the visible or near-infrared (NIR) spectrum. Known dyes useful in the present invention include carbocyanine, indocarbocyanine, oxacarbocyanine, thuicarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Organic dyes which are active in the NIR region are known in biomedical applications. However, there are only a few NIR dyes that are readily available due to the limitations of conventional dyes, such as poor hydrophilicity and photostability, low quantum yield, insufficient stability and low detection sensitivity in biological system, etc. Significant progress has been made on the recent development of NIR dyes (including cyanine dyes, squaraine, phthalocyanines, porphyrin derivatives and BODIPY (borondipyrromethane) analogues) with much improved chemical and photostability, high fluorescence intensity and long fluorescent life. Examples of NIR dyes include cyanine dyes (also called as polymethine cyanine dyes) are small organic molecules with two aromatic nitrogen-containing heterocycles linked by a polymethine bridge and include Cy5, Cy5.5, Cy7 and their derivatives. Squaraines (often called Squarylium dyes) consist of an oxocyclobutenolate core with aromatic or heterocyclic components at both ends of the molecules, an example is KSQ-4-H. Phthalocyanines, are two-dimensional 18π-electron aromatic porphyrin derivatives, consisting of four bridged pyrrole subunits linked together through nitrogen atoms. BODIPY (boron-dipyrromethane) dyes have a general structure of 4,4'-difluoro-4-bora-3a, 4a-diaza-s-indacene) and sharp fluorescence with high quantum yield and excellent thermal and photochemical stability.

Other imaging agents can include radioisotopes. Examples of isotopes useful in the present invention include Tc-94m, Tc-99m, In-111, Ga-67, Ga-68, Y-86, Y-90, Lu-177, Re-186, Re-188, Cu-64, Cu-67, Co-55, Co-57, Sc-47, Ac-225, Bi-213, Bi-212, Pb-212, Sm-153, Ho-166, or Dy-166.

In some embodiments the present invention provides the use of giant unilamellar vesicles for modeling cellular structures and functions. For example, the GUV of the present invention can comprise various and multiple protein and/or peptide components that together provide one or more known cellular functions. Examples include, but are not limited to, cellular machinery such as the Actin (ACTA) pathway, FKBP (FK506 binding protein) and FRB (FKBP-rapamycin binding) protein; other cellular receptor machinery, such as G-proteins, PIP$_2$ proteins, oncogene pathways, etc. The proteins can be labeled or ligated to labeled moieties to allow visualization of the components in response to external compounds, drugs, and the like.

In some embodiments the present invention provides the use of GUV for delivery of biologically active agents both in vitro and in vivo.

In accordance with an embodiment, the present invention provides a use of the giant unilamellar vesicles described herein, in an effective amount, to prepare a medicament, preferably for use as a medicament for treating a disease in a subject.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a disease in a mammal. Furthermore, the treatment or prevention provided by the inventive method can include treatment or prevention of one or more conditions or symptoms of the disease being treated or prevented. Also, for purposes herein, "prevention" can encompass delaying the onset of the disease, or a symptom or condition thereof.

As defined herein, in one or more embodiments, "administering" means that the one or more vesicles of the present invention are introduced into a sample having at least one cell, or population of cells, having a target gene of interest, and appropriate enzymes or reagents, in a test tube, flask, tissue culture, chip, array, plate, microplate, capillary, or the like, and incubated at a temperature and time sufficient to permit uptake of the luminal content of at least one of the vesicles of the present invention into the cytosol of the cell.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject. In some embodiments, a biologically active agent may be used in cross-linked polymer matrix of this invention, to, for example, promote cartilage formation. In other embodiments, a biologically active agent may be used in cross-linked polymer matrix of this invention, to treat, ameliorate, inhibit, or prevent a disease or symptom, in conjunction with, for example, promoting cartilage formation.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass genes that can be incorporated into the compositions of the invention. Non-limiting examples of biologically active agents include following: adrenergic blocking agents, anabolic agents, androgenic steroids, antacids, antiasthmatic agents, antiallergenic materials, anticholesterolemic and antilipid agents, anticholinergics and sympathomimetics, anticoagulants, anticonvulsants, antidiarrheal, anti-emetics, antihypertensive agents, anti-infective agents, anti-inflammatory agents such as steroids, non-steroidal antiinflammatory agents, antimalarials, antimanic agents, antinauseants, anti-neoplastic agents, anti-obesity agents, anti-parkinsonian agents, antipyretic and analgesic agents, anti-spasmodic agents, anti-thrombotic agents, antiuricemic agents, antianginal agents, antihistamines, antitussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and antithyroid agents, tranquilizers, uterine relaxants, vitamins, antigenic materials, and prodrugs.

Specific examples of useful biologically active agents the above categories include: anti-neoplastics such as androgen inhibitors, antimetabolites, cytotoxic agents, and immunomodulators; antitussives such as dextromethorphan, hydrobromide, noscapine, carbetapentane citrate, and chlophedianol hydrochloride; antihistamines such as chlorpheniramine phenindamine tartrate, pyrilamine doxylamine succinate, and phenyltoloxamine citrate; decongestants such as hydrochloride, phenylpropanolamine hydrochloride, pseudoephedrine hydrochloride, and ephedrine; various alkaloids such as codeine phosphate, codeine sulfate, and morphine; mineral supplements such as potassium chloride, zinc chloride, calcium carbonate, magnesium oxide, and other alkali metal and alkaline earth metal salts; ion exchange resins such as such as N-acetylprocainamide; antipyretics and analgesics such as acetaminophen, aspirin and ibuprofen; appetite suppressants such as phenyl-propanolamine or caffeine; expectorants such as guaifenesin; antacids such as aluminum hydroxide and magnesium hydroxide; biologicals such as peptides, polypeptides, proteins and amino acids, hormones, interferons or cytokines and other bioactive peptidic compounds, such as calcitonin, ANF, EPO and insulin; anti-infective agents such as antifungals, antivirals, antiseptics and antibiotics; and desensitizing agents and antigenic materials, such as those useful for vaccine applications.

More specifically, non-limiting examples of useful biologically active agents include the following therapeutic categories: analgesics, such as nonsteroidal anti-inflammatory drugs, opiate agonists and salicylates; antihistamines, such as H₁-blockers and H₂-blockers; anti-infective agents, such as antihelmintics, antianaerobics, antibiotics, aminoglycoside antibiotics, antifungal antibiotics, cephalosporin antibiotics, macrolide antibiotics, miscellaneous antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, antiretroviral agents, scabicides, and urinary antiinfectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and *vinca* alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, sympatholytics, sympathomimetics, and adrenergic agonist sympathomimetics; cardiovascular agents, such as antianginals, antianginals, calcium-channel blocker antianginals, nitrate antianginals, antiarrhythmics, cardiac glycoside antiarrhythmics, class I antiarrhythmics, class antiarrhythmics, class antiarrhythmics, class IV antiarrhythmics, antihypertensive agents, a-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, reductase inhibitor antilipemics, inotropes, cardiac glycoside inotropes, and thrombolytic agents; dermatological agents, such as antihistamines, anti-inflammatory agents, corticosteroid anti-inflammatory agents, anesthetics, topical antiinfectives, topical antiinfectives, antiviral topical antiinfectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H₂-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, antiandrogens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as antigout antiinflammatory agents, corticosteroid antiinflammatory agents, gold compound antiinflammatory agents, immunosuppressive anti-inflammatory agents, nonsteroidal antiinflammatory drugs, salicylate antiinflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, antiparkinsonian agents, antivertigo agents, opiate agonists, and opiate antagonists; ophthalmic agents, such as antiglaucoma agents, antiglaucoma agents, mitotics, antiglaucoma agents, mydriatics, adrenergic agonist mydriatics, antimuscarinic mydriatics, ophthalmic anesthetics, ophthalmic antiinfectives, ophthalmic aminoglycoside anti-infectives, ophthalmic macrolide antiinfectives, ophthalmic quinolone antiinfectives, ophthalmic sulfonamide antiinfectives, ophthalmic tetracycline antiinfectives, ophthalmic anti-inflammatory agents, ophthalmic corticosteroid antiinflammatory agents, and ophthalmic nonsteroidal anti-inflammatory drugs; psychotropic agents, such as antidepressants, heterocyclic antidepressants, monoamine oxidase inhibitors selective serotonin re-uptake inhibitors tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory antiinflammatory agents, and respiratory corticosteroid antiinflammatory agents; toxicology agents, such as antidotes, heavy agents, substance abuse agents, deterrent substance abuse agents, and withdrawal substance abuse agents; minerals; and vitamins, such as vitamin A, vitamin B, vitamin C, vitamin D, vitamin E, and vitamin K.

Other classes of biologically active agents from the above categories include: analgesics in general, such as lidocaine, other "caine" analgesics or derivatives thereof, and nonsteroidal anti-inflammatory drugs (NSAIDs) analgesics, including diclofenac, ibuprofen, ketoprofen, and naproxen; opiate agonist analgesics, such as codeine, fentanyl, hydromorphone, and morphine; salicylate analgesics, such as aspirin (ASA) (enteric coated ASA); H₁-blocker antihistamines, such as clemastine and terfenadine; H₂-blocker antihistamines, such as cimetidine, famotidine, nizadine, and ranitidine; anti-infective agents, such as mupirocin; antianaerobic antiinfectives, such as chloramphenicol and clindamycin; antifungal antibiotic antiinfectives, such as amphotericin b, clotrimazole, fluconazole, and ketoconazole; macrolide antibiotic antiinfectives, such as azithromycin and erythromycin; miscellaneous antibiotic antiinfectives, such as and imipenem; penicillin, antibiotic antiinfectives, such as nafcillin, oxacillin, penicillin G, and penicillin V; quinolone antibiotic anti-infectives, such as ciprofloxacin and nortfloxacin; tetracycline antibiotic antiinfectives, such as doxycycline, minocycline and tetracycline; antituberculosis antimycobacterial antiinfectives such as isoniazid and rifampin; antiprotozoal antiinfectives, such as atovaquone and dapsone; antimalarial antiprotozoal antiinfectives, such as chloroquine and pyrimethamine; antiretroviral antiinfectives, such as ritonavir and zidovudine; antiviral anti-infective agents, such as acyclovir, ganciclovir, interferon-γ, and rimantadine; alkylating antineoplastic agents, such as carboplatin and cisplatin; nitrosourea alkylating antineoplastic agents, such as carmustine (BCNU); antimetabolite antineoplastic agents, such as methotrexate;

pyrimidine analog antineoplastic agents, such as fluorouracil (5-FU) and gemcitabine; hormonal antineoplastics, such as goserelin, leuprolide, and tamoxifen; natural antineoplastics, such as aldesleukin, interleukin-2, docetaxel, etoposide, interferon; paclitaxel, other taxane derivatives, and tretinoin (ATRA); antibiotic natural antineoplastics, such as bleomycin, dactinomycin, daunorubicin, doxorubicin, and mitomycin; vinca alkaloid natural antineoplastics, such as vinblastine and vincristine; autonomic agents, such as nicotine; anticholinergic autonomic agents, such as benztropine and trihexyphenidyl; antimuscarinic anticholinergic autonomic agents, such as atropine and oxybutynin; ergot alkaloid autonomic agents, such as bromocriptine; cholinergic agonist parasympathomimetics, such as pilocarpine; cholinesterase inhibitor parasympathomimetics, such as pyridostigmine; α-blocker sympatholytics, such as prazosin; β-blocker sympatholytics, such as atenolol; adrenergic sympathomimetics, such as albuterol and dobutamine; cardiovascular agents, such as aspirin (ASA) (enteric coated ASA); β-blocker antianginals, such as atenolol and propranolol; calcium-channel blocker antianginals, such as nifedipine and verapamil; nitrate antianginals, such as isosorbide dinitrate (ISDN); cardiac glycoside antiarrhythmics, such as class I antiarrhythmics, such as lidocaine, mexiletine, phenytoin, procainamide, and quinidine; class antiarrhythmics II, such as atenolol, metoprolol, propranolol, and timolol; class III antiarrhythmics, such as amiodarone; class IV antiarrhythmics, such as diltiazem and verapamil; antihypertensives, such as prazosin; angiotensin-converting enzyme inhibitor (ACE inhibitor) antihypertensives, such as captopril and enalapril; antihypertensives, such as atenolol, metoprolol, nadolol, and propanolol; calcium-channel blocker antihypertensive agents, such as diltiazem and nifedipine; central-acting adrenergic antihypertensives, such as clonidine and methyldopa; diuretic antihypertensive agents, such as amiloride, furosemide, hydrochlorothiazide (HCTZ), and spironolactone; peripheral vasodilator antihypertensives, such as minoxidil; antilipemics, such as gemfibrozil and probucol; bile acid sequestrant antilipemics, such as cholestyramine; reductase inhibitor antilipemics, such as lovastatin and pravastatin; inotropes, such as amrinone, dobutamine, and dopamine; cardiac glycoside inotropes, such as thrombolytic agents, such as alteplase, anistreplase, streptokinase, and urokinase; dermatological agents, such as colchicine, isotretinoin, methotrexate, minoxidil, tretinoin dermatological corticosteroid anti-inflammatory agents, such as betamethasone and dexamethasone; antifungal topical antiinfectives, such as amphotericin clotrimazole, miconazole, and nystatin; antiviral topical antiinfectives, such as acyclovir; topical antineoplastics, such as electrolytic and renal agents, such as lactulose; loop diuretics, such as furosemide; potassium-sparing diuretics, such as triamterene; thiazide diuretics, such as hydrochlorothiazide (HCTZ); uricosuric agents, such as probenecid; enzymes and thrombolytic enzymes, such as alteplase, anistreplase, streptokinase and urokinase; antiemetics, such as prochlorperazine; salicylate gastrointestinal anti-inflammatory agents, such as sulfasalazine; gastric acid-pump inhibitor anti-ulcer agents, such as omeprazole;) H$_2$-blocker anti-ulcer agents, such as cimetidine, famotidine, nizatidine, ranitidine; digestants, such as pancrelipase; prokinetic agents, such as erythromycin; opiate agonist intravenous anesthetics such as fentanyl; hematopoietic antianemia agents, such as (G-CSF), and (GM-CSF); coagulation agents, such as factors 1-10 (AHF 1-10); anticoagulants, such as warfarin; thrombolytic enzyme coagulation agents, such as alteplase, anistreplase, streptokinase and urokinase; hormones and hormone modifiers, such as bromocriptine; abortifacients, such as methotrexate; antidiabetic agents, such as insulin; oral contraceptives, such as estrogen and progestin; progestin contraceptives, such as levonorgestrel and norgestrel; estrogens such as conjugated estrogens, diethylstilbestrol (DES), estrogen (estradiol, estrone, and estropipate); fertility agents, such as clomiphene, human chorionic gonadotropin (HCG), and menotropins; parathyroid agents such as calcitonin; pituitary hormones, such as desmopressin, goserelin, oxytocin, and vasopressin (ADH); progestins, such as medroxyprogesterone, norethindrone, and progesterone; thyroid hormones, such as levothyroxine; immunobiologic agents, such as interferon beta-1b and interferon gamma-1b; immunoglobulins, such as immune globulins IgM, IgG, IgA; amide local anesthetics, as lidocaine; ester local anesthetics, such as benzocaine and procaine; musculoskeletal corticosteroid antiinflammatory agents, such as beclomethasone, betamethasone, cortisone, dexamethasone, hydrocortisone, and prednisone; musculoskeletal anti-inflammatory immunosuppressives, such as azathioprine, cyclophosphamide, and methotrexate; musculoskeletal nonsteroidal anti-inflammatory drugs such as diclofenac, ibuprofen, ketoprofen, ketorlac, and naproxen; skeletal muscle relaxants, such as and diazepam; reverse neuromuscular blocker skeletal muscle relaxants, such as pyridostigmine; neurological agents, such as nimodipine, riluzole, tacrine and ticlopidine; anticonvulsants, such as carbamazepine, gabapentin, lamotrigine, phenytoin, and valproic acid; barbiturate anticonvulsants, such as phenobarbital and primidone; benzodiazepine anticonvulsants, such as clonazepam, diazepam, and lorazepam; anti-Parkinson's' agents, such as bromocriptine, levodopa, carbidopa, and pergolide; anti-vertigo agents, such as meclizine; opiate agonists, such as codeine, fentanyl, hydromorphone, methadone, and morphine; opiate antagonists, such as naloxone; antiglaucoma agents, such as timolol; mitotic anti-glaucoma agents, such as pilocarpine; ophthalmic aminoglycoside antiinfectives, such as gentamicin, neomycin, and tobramycin; ophthalmic quinolone antiinfectives, such as ciprofloxacin, norfloxacin, and ofloxacin; ophthalmic corticosteroid anti-agents, such as dexamethasone and prednisolone; ophthalmic nonsteroidal anti-inflammatory drugs such as diclofenac; antipsychotics, such as clozapine, haloperidol, and risperidone; benzodiazepine anxiolytics, sedatives and hypnotics, such as clonazepam, diazepam, lorazepam, oxazepam, and prazepam; psychostimulants, such as methylphenidate and pemoline; such as codeine; bronchodilators, such as adrenergic agonist bronchodilators, such as albuterol; respiratory corticosteroid antiinflammatory agents, such as dexamethasone; antidotes, such as flumazenil and naloxone; heavy metal agents, such as penicillamine; deterrent substance abuse agents, such as disulfiram, naltrexone, and nicotine; withdrawal substance abuse agents, such as bromocriptine; minerals, such as iron, calcium, and magnesium; vitamin B compounds, such as cyanocobalamin (vitamin B12) and niacin (vitamin B3); vitamin C compounds, such as ascorbic acid; and vitamin D such as calcitriol.

Further, recombinant or cell-derived proteins may be used, such as recombinant beta-glucan; bovine immunoglobulin concentrate; bovine superoxide dismutase; formulation comprising fluorouracil, epinephrine, and bovine collagen; recombinant hirudin (r-Hir), HIV-1 immunogen; recombinant human growth hormone recombinant EPO (r-EPO); gene-activated EPO (GA-EPO); recombinant human hemoglobin (r-Hb); recombinant human mecasermin (r-IGF-1); recombinant interferon α; lenograstim (G-CSF); olanzapine; recombinant thyroid stimulating hormone (r-TSH); and topotecan.

Still further, the following listing of peptides, proteins, and other large molecules may also be used, such as interleukins 1 through 18, including mutants and analogues; interferons a, y, and which may be useful for cartilage regeneration, hormone releasing hormone (LHRH) and analogues, gonadotropin releasing hormone transforming growth factor (TGF); fibroblast growth factor (FGF); tumor necrosis factor-α); nerve growth factor (NGF); growth hormone releasing factor (GHRF), epidermal growth factor (EGF), connective tissue activated osteogenic factors, fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-a-y-globulin; superoxide dismutase (SOD); and complement factors, and biologically active analogs, fragments, and derivatives of such factors, for example, growth factors.

Members of the transforming growth factor (TGF) supergene family, which are multifunctional regulatory proteins, may be incorporated in a polymer matrix of the present invention. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (lGF)), (for example, lnhibin A, lnhibin B), growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

As used herein, the term "treat," as well as words stemming there from, includes preventative as well as disorder remitative treatment. The terms "reduce," "suppress," "prevent," and "inhibit," as well as words stemming there from, have their commonly understood meaning of lessening or decreasing. These words do not necessarily imply 100% or complete treatment, reduction, suppression, or inhibition.

As defined herein, in one or more embodiments, "administering" means that the one or more GUV of the present invention are introduced into a sample having at least one cell, or population of cells, having a target gene of interest, and appropriate enzymes or reagents, in a test tube, flask, tissue culture, chip, array, plate, microplate, capillary, or the like, and incubated at a temperature and time sufficient to permit uptake of the at least one GUV of the present invention into the cytosol, where it affect the target gene of interest and in the at least one cell or population of cells.

In another embodiment, the term "administering" means that at least one or more GUV of the present invention are introduced into a subject, preferably a subject receiving treatment for a disease, and the at least one or more GUV are allowed to come in contact with the one or more disease related cells or population of cells having the target of interest in vivo.

In an embodiment, the present invention provides a GUV composition comprising one or more GUV microparticles, in an effective amount, wherein the composition includes a pharmaceutically and physiologically acceptable carrier In another embodiment, the present invention provides the use of a GUV composition comprising one or more GUV microparticles, in an effective amount, wherein the composition includes a pharmaceutically and physiologically acceptable carrier, to prepare a medicament, preferably for use as a medicament for treating a disease in a subject.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

It is contemplated that any of the GUV embodiments of the present invention described above can also encompass a pharmaceutical composition comprising the GUV and a pharmaceutically acceptable carrier.

With respect to GUV compositions described herein, the carrier can be any of those conventionally used, and is limited only by physico-chemical considerations, such as solubility and lack of reactivity with the active compound (s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

The choice of carrier will be determined, in part, by the particular GUV containing composition, as well as by the particular method used to administer the composition. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, PA, Banker and Chalmers, eds., pages 238-250 (1982), and *ASHP Handbook on Injectable Drugs*, Trissel, 15th ed., pages 622-630 (2009)).

For purposes of the invention, the amount or dose of the GUV of the present invention that is administered should be sufficient to effectively target the cell, or population of cells in vivo, such that the modulation of the expression of the target gene of interest can be detected, in the subject over a reasonable time frame. The dose will be determined by the efficacy of the particular GUV formulation and the location of the target population of cells in the subject, as well as the body weight of the subject to be treated.

The dose of the GUV of the present invention also will be determined by the existence, nature and extent of any adverse side effects that might accompany the administration of a particular GUV. Typically, an attending physician will decide the dosage of the GUV with which to treat each individual subject, taking into consideration a variety of factors, such as age, body weight, general health, diet, sex, compound to be administered, route of administration, and the severity of the condition being treated. By way of example, and not intending to limit the invention, the dose of the GUV of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the GUV of the present invention can be at a concentration from about 1 nM to about 10,000 nM, preferably from about 10 nM to about 5,000 nM, more preferably from about 100 nM to about 500 nM.

EXAMPLES

The following embodiments provide guidance in the various choices made prior to GUV fabrication and the overview of the implementation of the steps are presented.

1a. Considerations with the Luminal Content

The choice of material to be encapsulated in the GUV is a key design consideration. For example, when studying biological signaling pathways, or interrogation of protein-lipid interaction, etc. the chosen materials are usually a purified protein or a combination of several proteins. When using detectable moieties, these materials can include, for example, a fluorescent molecule of choice. Alternatively, if GUV are desired for targeted delivery, e.g., delivery of DNA, RNA, small molecules or drugs, encapsulation of which inside the GUVs can be used. It is recommended that all the starting material to be brought to relatively high initial concentrations so that: 1) Post-fabrication, their local concentration is still high enough to yield the desired function; and 2) The other buffer components that contribute to GUV stability do not become diluted as the result of material encapsulation. Specifically, the volume of the fraction that constitutes the luminal content is anywhere between about 60 µl to 120 µl. The relatively high concentration of the starting material compensates for the relatively low volumetric content, and thus guarantees that the desired concentration of the specific material that is to serve a specific function is present. However, these concentrations are context-dependent. For example, the final concentrations of certain encapsulated contents, such as drugs or proteins, should still be low enough to avoid adverse effects.

In general, in the case of protein embodiments, if a mixture of proteins in certain buffers are to be encapsulated, the concentration of each of these proteins individually should be high enough to account for the dilution effect during assembly of luminal content. However, the protein stock concentrations will differ depending on the protein used, as the aggregation tendencies of proteins vary. In general, for the case of proteins, the final concentration of reconstituted proteins in GUV lumen or membrane ranges between 20 nM to 20 µM for most applications. This concentration is generally within the physiological concentration range of most proteins either in mammalian cells or in the in vitro test tube studies reported.

The same concentration ranges apply to fluorescent dyes, drugs, DNA, small molecules, etc. that are being encapsulated. However, these small molecules are less prone to aggregation and higher concentrations of them in the rage of 10 nM to 1 mM can be easily reconstituted in the GUVs. For example, most commercially available dyes are bright enough to be visualized at the low µM concentration range.

For embodiments comprising in vitro transcription, translation reconstitution or delivery of synthetic gene circuits, oligonucleotides in the nM to µM concentration range, depending on the reaction, are generally deemed sufficient. In sum, it is crucial to note that the recommendation for the maximum initial concentration of the luminal material also in part stems from stability considerations. It is also understood that the higher the final molar concentration of the sucrose (one of the components that is intended to balance the osmotic pressure and thus the mechanical integrity of the GUVs) encapsulated in the lumen, the more stable the GUVs. Thus, it is ideal that only few microliters of the desired functional material (protein, DNA, drug, etc.) is diluted in sucrose supplemented with the buffer of choice. Finally, for applications where is it is difficult to accurately determine the concentration of the starting material, iterations of the experiment with various volumes of the material can point to the range of concentrations desired. This particularly applies to encapsulation of cell lysates, where the population of molecules is heterogonous and concentration assessment are therefore difficult.

In some embodiments, a micro-osmometer can be used to more accurately measure the osmolarity and the molar concentration of the inner or outer GUV solution, ascertaining that these concentrations match before starting the fabrication process. If a cell lysate is to be encapsulated in the GUVs, the use of any detergent-containing buffers (e.g. RIPA buffer) during the extraction and preparation procedure should be avoided, or at least any trace of detergent in the final buffer containing the cell extract should be removed, before GUV fabrication.

2. Considerations with Osmotic Pressure

The reaction to be reconstituted inside the GUVs is prepared by mixing the desired amount of molecule(s) of interest with about 0.5 M to about 5 M sucrose, preferably about 1 M sucrose, for a total volume of about 10 μl to 120 μl. The volume of the material used is dictated by the final concentration of the content required for the experiment. The osmotic pressure of this solution (denoted as X) must be calculated or measured with a micro-osmometer in order to determine the molar concentration of the glucose (X) that will engulf the vesicles.

In general, GUV are devoid of cytoskeleton structures such as actin and microtubules, leading to their fragility. Therefore, GUVs are sensitive to disparities between inter- and extra-vesicular osmotic pressure. Given a known concentration of proteins and buffer components to be reconstituted, balancing this osmotic pressure can be achieved. Osmotic pressure or $\pi$ of an aqueous solution is calculated as $\pi=MRT$ where M is the molar concentration of the reconstituted components, R is the ideal gas constant, and T is the temperature in Kelvin scale. Therefore given experimental conditions, the only variable of note is molar concentration M which should be balanced between the inner and outer solutions to assure the mechanical integrity of the vesicles. In the situation where this molar concentration is not known, osmotic pressure can be measured using a micro-osmometer 3a. Choice of Inner and Outer Leaflet Lipids After choosing the luminal content, the selection of a suitable combination of lipids for both inner and outer leaflet of the GUV should be decided. In general, depending on the type of membrane that is being duplicated, the lipid combinations are selected to comport with the native membrane composition. However, in cases where: 1) Encapsulation of biological material within the lumen of a vesicle is of interest; and 2) The exact lipid composition is not of concern; the use of 100% chicken egg-PC (phosphatidylcholine extracted from egg) for both inner and outer leaflets can be used. Higher GUV yield is typically found using this lipid composition. Furthermore, phosphatidylcholine is abundant in every cell of the human body which makes this lipid a biologically compatible option. Lastly, the neutrally charged phosphatidylcholine lipids do not exhibit electrostatic interaction with the luminal content, thus reducing the chance of inner content-lipid interaction. For example, based on the inventors' observations, some neutrally charged proteins can have unspecific affinity for negatively charged lipids (e.g., PS). Similarly, at times proteins that do not contain a histidine tag showed affinity for DGS-Ni conjugated lipids. These nonspecific protein-lipid interactions call for additional efforts in optimizing the lipid and protein concentrations, such that localization of the proteins is correct and that the desired reaction occurs in the GUVs.

In accordance with some protein encapsulation embodiments, those proteins with neutral charge and hydro-affinity are expected to localize at the lumen of the GUV at physiological pH levels. However, it was found that it is possible to harness the electrostatic interactions between charged proteins and lipids to anchor otherwise luminal proteins to the membrane of the vesicles. These methods require fusing the proteins with tags such as a poly-histidine sequence (His-tag), which facilitates interaction with the Nickel-conjugated lipids (DGS-NTA(Ni)). Alternatively, using positively charged peptide domains, such as myristoylated alanine-rich protein kinase C substrate (MARCKS), or the C2 domain of the lactadherin (lact-C2), and in turn, using negatively charged lipids such as phosphatidylserine (PS), and phosphatidylinositol 4,5-bisphosphate or ($PIP_2$) in the inner leaflet of the vesicles facilitated protein-lipid interaction.

In some embodiments, on can use PS, $PIP_2$ or DGS-Ni in conjunction with phosphotidylcholine. The w/w of ratio of these lipids to the PC counterparts is recommended to be <5 to about 95 to optimize GUV yield. For cases when only a handful of GUVs are needed for the study this is not a concern. But a high yield GUV preparation, desired for most applications, would result in formation of 10-1000 GUVs in an Eppendorf tube vial. It is best to increase the PC concentration and it is also crucial to supplement the outer leaflet with the same weight concentration of negatively charged lipids or DGS-Ni, if such lipids are used in the inner leaflet (i.e. symmetric vesicles are more easily fabricated). This specially applies in the case of encapsulating membrane-bound proteins where charged lipids in the outer leaflet of the GUVs are crucial.

While not being held to any particular theory, it is thought that the electrostatic interaction between the lipids and the ensuing impact on the membrane geometry and structure plays a role. It is of note that $PIP_2$ was found to precipitate out of the oil solution within minutes at room temperature, and thus, its use for exclusively harnessing its charge is not recommended.

Pertaining to the selection of the lipids, it is also important for the melting temperatures of the lipids to be compatible with each other. The melting temperature of lipids is an indicator of their solubility at various temperature conditions, and is partly dictated by the saturation condition of the lipids. The melting point of unsaturated fatty acids is typically lower than for saturated fatty acids. The melting point is also an important indicator of the lipid solubility in the solvent of choice.

Thus, in accordance with some embodiments, it is important to select a combination of lipids whose melting point is above room temperature and within +/−20° C. of each other. For example, the transition temperature of 16:0-18:1 PC (POPC) at −2° C. while the transition temperature of 16:0-18:1 PS (POPS) is at 14° C. Therefore, if these lipids are solubilized together they are both expected to be in the soluble, liquid form at room temperature (25° C.). Thus, this lipid combination is suitable for applications or experiments performed at room temperature. For solubilization purposes however, heating lipids to temperatures as high as 65° C. is recommended for this lipid combination. These recommended solubilization temperatures are generally experimentally optimized. In contrast 16:0 PC (DPPC) has a melting point of 41° C., and thus neither alone nor in combination with PS would it be soluble at room temperature.

In some embodiments, the solvents used to dissolve the lipids are typically commercially available small chain solvents such as chloroform or methanol, however other organic solvents may be used, including, methylene chloride, carbon tetrachloride, dimethyl formamide, ethanol, acetonitrile, hexane, and the like.

Depending on the saturation condition of the lipid chain and the size of the lipid heads, placement of a certain combination of lipids in form a vesicle might not be geometrically possible or it might cause instability in lipid assembly (FIG. 1). Therefore, prior to proceeding with reconstitution of any proteins or extracts that could further complicate the GUV formation, it is recommended to make vesicles encapsulating water-solubilized dyes such as TRITC or FITC dextran.

3b. Aliquoting the Lipids for the Inner and Outer Leaflets

In case of asymmetric vesicles, one would first prepare a first vial, which typically would be any container suitable for use with lipids where the lipids cannot adhere to the inner walls of the container, such as the use of a silanized amber screw top glass bottle for use with the inner lipid mixture, and a second vial for use with the outer lipid mixture.

Using a pipette or micro-syringe, an aliquot of about 5 mg of solvent (e.g., chloroform- or methanol)-solubilized lipids are place in vials. The rest of the vial is filled with a flow of nitrogen or argon stream. The tubes are capped, for example using Parafilm or Teflon tape to seal, and can be stored at −20° C. for up to 6 months. When preparing leaflet membranes with multiple lipid types, the solvent solubilized lipids are mixed at the desired ratio to a total of 5 mg per vial. The lipids are dried for about 12 hours or overnight in a vacuum desiccator.

3c. Lipid Solubilization

To the dried lipids described above, a long chain nonpolar solvent solution such as hexadecane is mixed with: silicon oil (9/1 V/V %) (about 4.8 ml total) for a final lipid concentration of about between 0.5 to 2 mg/ml, preferably about 1.04 mg/ml. The type of the solvent and the volume of it varies depending on the lipid combination used and had to be experimentally optimized.

In some embodiments, a combination of about 100% heavy mineral oil combined with either 100% POPC or egg-PC lipids can also be used. Furthermore, the same lipids can also be solubilized in 100% hexadecane, or 9:1 V/V hexadecane:silicon oil. If the oil artifacts at the lipid bilayer interface are a concern, it is recommended to reduce the silicon oil volume to the minimum necessary for solubilization.

Other oils suitable for use in testing the solubility include: light mineral oil, paraffin oil, squalene, and decane. The vials are then capped and sealed with Teflon tape and Parafilm. The vials are then placed in an oven at 65° C., where the samples are rotated for about 8 rpm for 3 hours. In some embodiments, filling the glass vial to its nearly maximum capacity of 5 ml, and refraining from harsh agitation of the lipids, minimizes lipid oxidation during solubilization. In some embodiments, it is preferred to have a space of about 100-200 µl in volume at the top of the lipid vial to account for thermal expansion, otherwise the lipids spill or the glass vial can break due to pressure build up. In some embodiments, when working with membrane bound proteins or charged lipids, hexadecane is recommended. While with the other applications lipids solubilized in heavy mineral oil, paraffin oil, or a combination of either and squalene GUVs can also be used.

3d. Vesicle Outer Leaflet Assembly

In an embodiment, using 1.5 ml tubes, add about 350 µl of the calculated concentration (X mM) of glucose and gently pipette about 200-350 µl of the solubilized outer leaflet lipid mixture that is cooled to room temperature on top. The mixture is incubated undisturbed at room temperature for a minimum of about 5 minutes to form a monolayer of outer lipid leaflet on top of the glucose. Avoiding any disturbance of the lipid on glucose solution is critical to monolayer formation. The recommended volumes and concentrations are optimized for the surface area of the glucose-lipid interface at the 200-350 µl volume mark of a 1.5 ml capacity Eppendorf tube. If the assembly reaction is scaled up or down, the volume and concentration values reported here can be re-optimized given the size of the tube. To do so, based on how the reaction is scaled up/down the volume of the outer buffer solution is determined. Once this volume of buffer is added to the solution, the cross sectional area of the tube where it is added is calculated. Considering the surface area of the lipid heads in the outer lipid bilayer one can determine how many lipid heads are needed to completely pack the tube cross sectional area calculated. Correspondingly this determines the concentration of the lipid solution that will be placed on top of the buffered glucose (the volume of the lipids should be matching that of the glucose solution). If lipids are supplied in excess, then it is not guaranteed that the GUVs will be unilamellar. If there are too few lipids supplied they will not cover the entire glucose solution surface and the GUVs will not be formed.

4. Emulsion Phase Preparation

In an exemplary embodiment, a 1.5 ml Eppendorf tube is filled with about 1.2 ml of 1 mg/ml lipid in oil mixture. About 10-100 µl of the luminal content prepared above (for smaller vesicles use lower volumes) is then added to the mixture. The tip of the tube must be agitated with the largest force possible ~10 times until you see a completely homogenous turbid mixture. It is better to minimize the number of pulses, and maximize the force so that lipid oxidation is minimized.

5. GUV Formation and Imaging

About 200-300 µl of the emulsion from above is added on top of the outer leaflet tube set up in the vesicle outer leaflet assembly step. The mixture is then centrifuged at 2500×g for about 6 min. The bottom of the tube is then punctured with a needle to collect the GUVs from the lower layer. One must not collect the oil as it will rupture the collected GUVs. About 100 µl of the collected GUVs are transferred to an 8-well plate for imaging. Depending on the final concentration of glucose used in the outer solution the vesicle sedimentation time differs. For concentrations greater than approximately 700 mM glucose within few minutes the GUVs settle to the bottom of the chamber where they can remain in focus.

Example 1

Figure 3A:
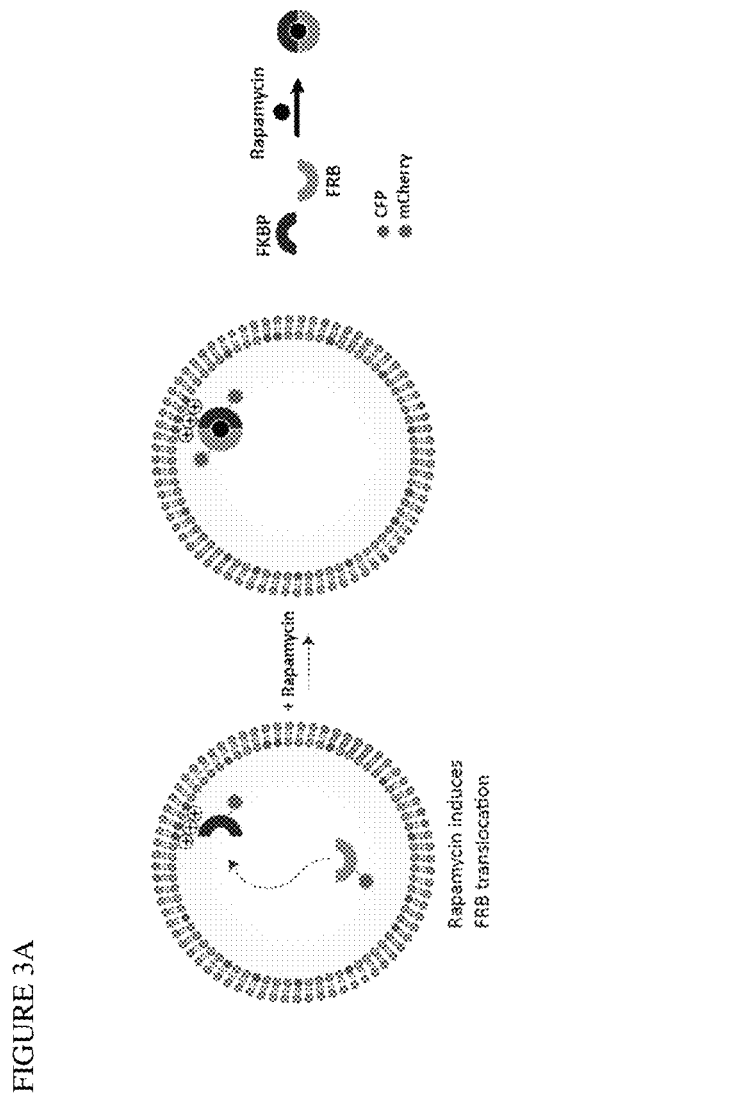
FIGS. 3A-3B. A depiction of an embodiment of the GUV of the present invention where the internal components can be affected by external stimuli. GUV encapsulating chemically inducible dimerization protein components which exhibit a shift in protein localization as the externally applied drug rapamycin crosses the vesicular membrane. 3A) Schematic of the GUV containing fluorescently-labeled FK506 binding protein (FKBP) and FKBP-rapamycin binding (FRB) proteins. In this embodiment, FKBP peptide is fused to the positively charged myristoylated alanine-rich protein kinase c substrate (MARCKS) domain and binds to the negatively charged phosphatidylserine lipids present at the inner leaflet. The FKBP binding partner, FRB, is luminal. Once the externally administered rapamycin permeates the GUV membrane, the luminal FRB heterodimerizes with the membrane-anchored FKBP protein. This results in shifting the localization of FRB-fused protein from the lumen to the membrane. 3B) Epi-fluorescent images of GUVs containing fusion FKBP and FRB proteins before and after administration of rapamycin or the DMSO vehicle. i). Prior to rapamycin addition mCherry-FKBP-MARCKS localizes at the membrane while CFP-FRB is luminal. Once rapamycin is administered, the FRB-containing construct translocates towards the membrane where its binding partner, FKBP, is tethered. ii) In the control, the localizations of the FKBP- and FRB-containing fusion proteins do not change once the vehicle (DMSO) is administered, highlighting that the protein localization shift is rapamycin-dependent. The normalized intensity profiles are the intensity traces of the dashed line in each image. Scale bar is 10 μm.
Figure 3B:
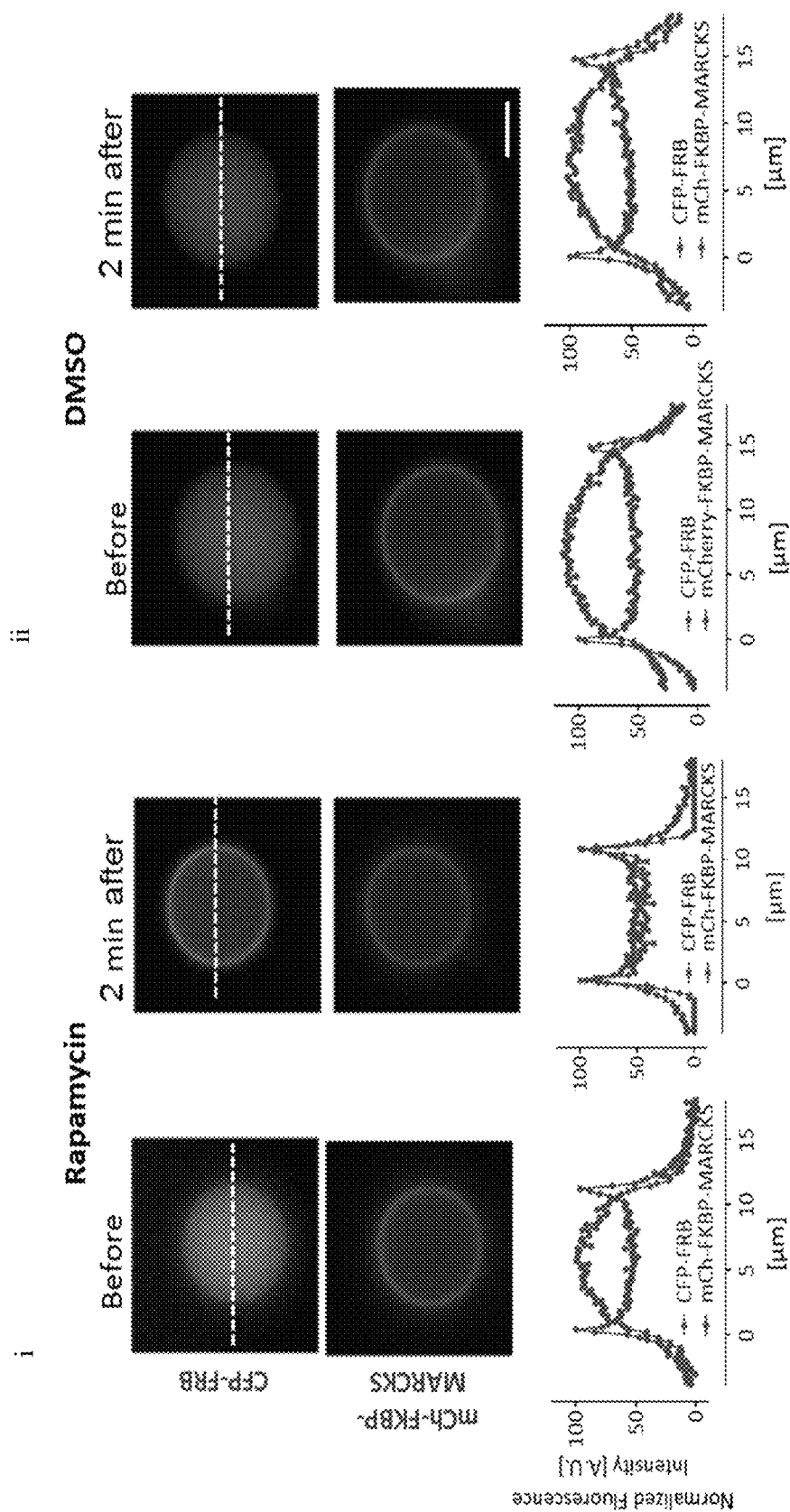

Various dextran dyes and soluble fluorescent proteins were encapsulated to optimize robust fabrication of vesicles with luminal content. The fabrication process was then adapted to allow for encapsulation of membrane-bound protein components as well. This was accomplished by fusing the MARCKS domain to the protein of choice and in turn using the PS or $PIP_2$ lipids in the inner leaflet. Moreover, an exemplary system was assembled where the localization of the protein content could be shifted from the lumen to the membrane on demand by adding rapamycin that permeates the vesicles (FIG. 3). This was achieved by using the chemically inducible dimerization paradigm where FKBP (FK506 binding protein) and FRB (FKBP-rapamycin binding) protein can hetrodimerize in the presence of rapamycin. At the initial time point, mCh-FKBP-MARCKS is anchored at the membrane and the CFP-FRB is luminal. However, upon rapamycin administration, the CFP-FRB translocated towards the membrane where its FKBP binding partner resides. This highlights vesicle stability in the presence of external chemicals. It also signifies the permeability of these vesicles to drugs and other small molecules, exhibiting a cell-like feature. The shift in localization of proteins from the 3D lumen to the 2D membrane allows for enrichment of peptide content at the membrane in real time. This is due to the diminishment of the surface to volume ratio at larger radial lengths.

Example 2

GUV coupled with the chemically inducible dimerization system were used to change the localization of the encapsulated peptides at will. This method and resulting composition was used to assemble a mimetic Rac1 signaling pathway in the artificial cells.

Ras-related C3 botulinum toxin substrate (Rac) is a member of the RAS family of small GTPases. Rac proteins are highly plastic in terms of subcellular localization, regulation, and crosstalk with other signaling pathways, and thus, serve as a regulation point of many cellular processes. For instance, active Rac1 triggers activation of a large variety of downstream effectors, leading to signaling events controlling protein trafficking, antimicrobial cytotoxicity, glucose transport, cytoskeleton rearrangement, and directed motility. Particularly, Rac1 is known as the master regulator of cell motility and is key in tumor angiogenesis, invasion, and metastasis. Thus, Rac1 inhibitors are of interest given their potential as therapeutic targets. As such, elucidating the mechanism of Rac1 function and interaction with other regulatory molecules is of great interest and importance.

Figure 4A:
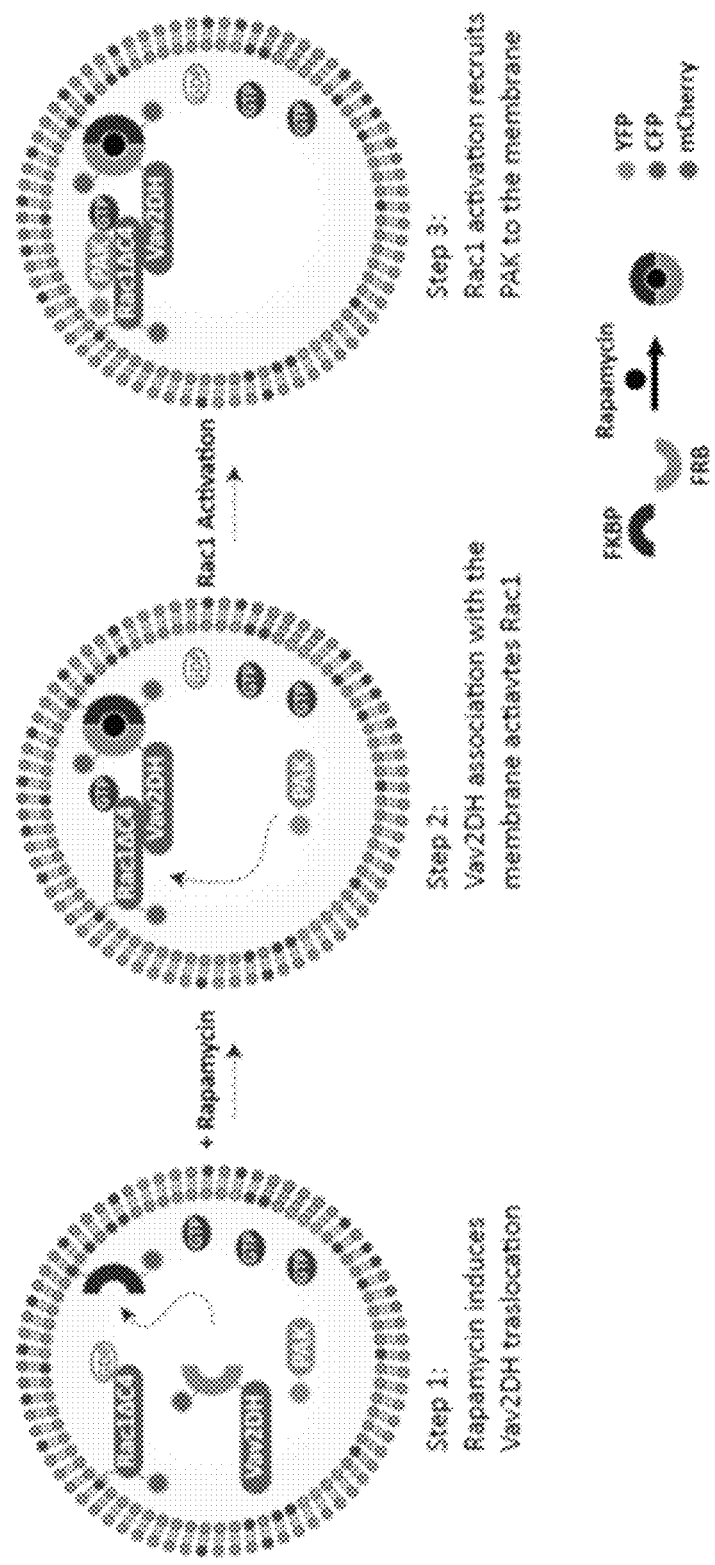
FIGS. 4A-4C. A depiction of another embodiment where GUV containing four different protein constructs used to assemble an externally triggerable mimetic signaling pathway in the GUV. In this embodiment, the signaling event of choice, Rac1 activation, is induced and detected in GUVs in real-time. 4A) Schematic of the GUV containing Hisx6-mCherry-FKBP and mCherry-Rac1WT-Hisx8 both anchored at the membrane using DGS-NTA (Ni) conjugated lipids. The Vav2 protein DH domain that activates Rac1 and is fused to CFP and FRB and has luminal localization. The Rac1 activity sensor, PAK1, is fused to YFP and is also luminal. Upon rapamycin administration, Vav2DH translocation towards the membrane favors the nucleotide loading state of Rac1 from Rac1-GDP to Rac1-GTP which is the state that can activate downstream substrates. This reaction, in turn, triggers accumulation of the Rac1-GTP effector, YFP-PAK1, to the membrane. 4B-C) The shift in the localization of the Rac1 activator and sensor in the presence of externally administered rapamycin as observed by confocal microscopy. 4B) The localization of the Hisx6-mCh-FKBP and mCherry-Rac1WT-Hisx8 are both at the membrane prior- and post-rapamycin administration. The localization of CFP-FRB-Vav2DH changes from the luminal state to the membrane-bound state in the presence of rapamycin, thus activating Rac1 at the membrane. This leads to the ensuing shift of the localization of the YFP-PAK1 effector from the lumen to the membrane. 4C) CFP-FRB-Vav2DH and PAK1 remain luminal before and after DMSO addition, indicating that the Rac1 activation could only be achieved once the local concentration of Vav2DH is enriched at the membrane using the external rapamycin trigger.
Figures 4B, 4C:
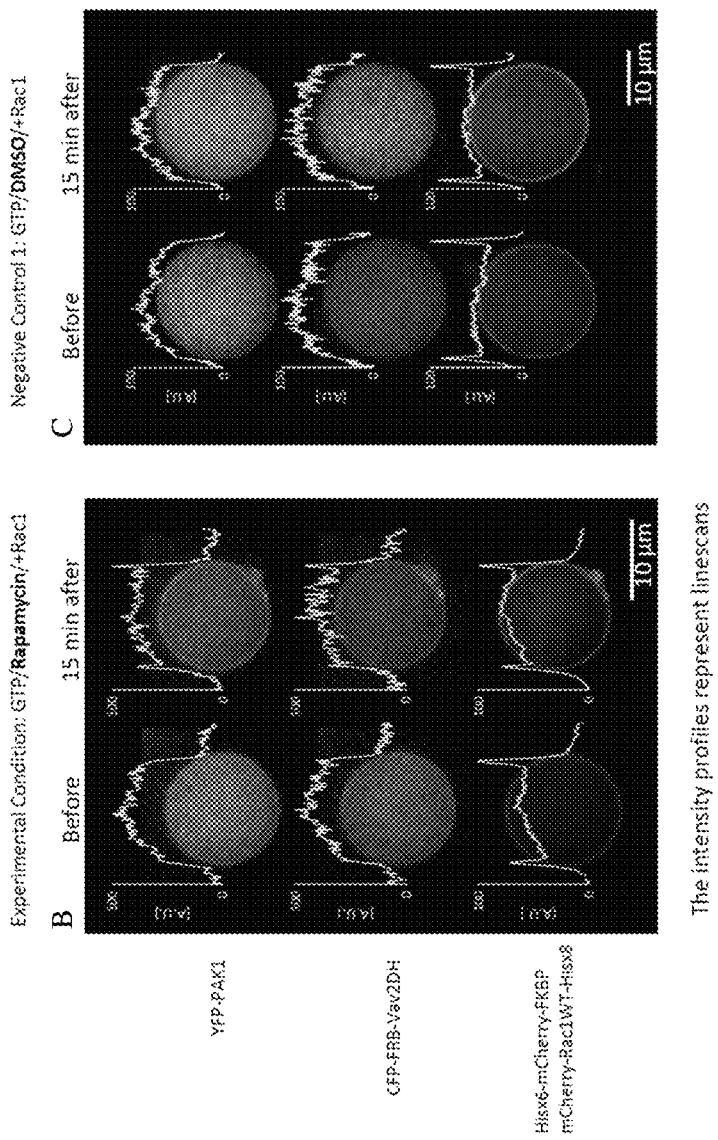
Figures 5A, 5B, 5C, 5D:
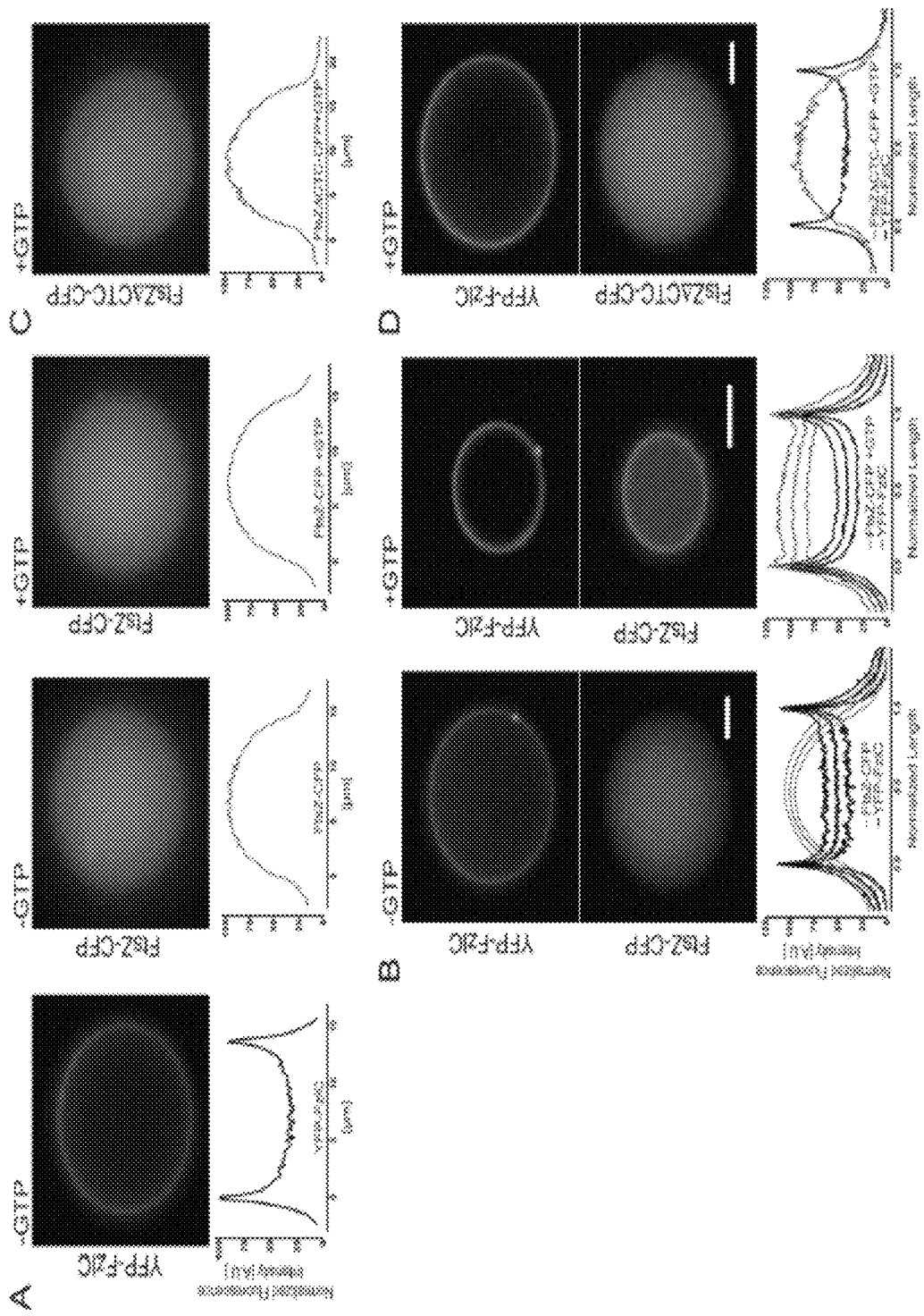
FIGS. 5A-5D. YFP-FzlC recruits FtsZ-CFP polymers to membranes inside giant unilamellar vesicles (GUV). Fluorescence micrographs of representative GUVs containing the indicated proteins +/−GTP.

Previous studies have revealed that Rac1 GTPases exhibit switch-like behavior and fluctuate between an inactive GDP-bound state and the active GTP-state. Proteins such as guanine exchange factors or GEFs (i.e. T-lymphoma invasion and metastasis-inducing protein (Tiam1), Vav2, etc.) promote the exchange of GDP for GTP on Rac1, and put Rac1 in an active state. In contrast, the GTPase-activating proteins or GAPs (i.e. breakpoint cluster region (BCR), B-chimaerin, etc.) promote hydrolysis of the bound GTP molecule and revert Rac1 to back its inactive state. Another important component in Rac1 regulation is Rac1 docking at the plasma membrane where an array of biological processes are regulated. The CAAX motif and the polybasic residues intrinsic to the Rac1 c-terminus achieve Rac1 membrane localization. Reports of cell-based Rac1 studies are known and show the spatiotemporal regulation of Rac1 in a complete molecular landscape where all the regulatory elements are present. However, in these previous studies, it was impossible to decouple the key regulators and extract the order of signaling events, mainly due to the complexity and redundancy in the signaling pathways intertwined within a cell in its entirety. In some studies, a minimal in vitro assay was used to complement such cell-based studies in that few signaling proteins are interrogated in a bulk solution. However, these minimal systems lost the aspect of the signaling that is a direct function of cell geometry and signaling localization in confined spaces such as cell membrane. This is specifically the case for Rac1 protein. The utilization of the GUV platform of the present invention, is the first report of bridging these two classes of studies. By using a membrane-bound compartment and enriching the localization of a GEF activator such as Vav2 Dbl homology domain (Vav2DH) at the GUV inner membrane, Rac1 residing at the membrane becomes active. This in turn recruits the downstream Rac1 effector, PAK1 protein CRIB (Cdc42 and Rac-interactive binding) domain, to the membrane. This Rac1 mimetic pathway is achieved using the GUV of the present invention (FIG. 4). Furthermore, the present invention allows for the rigid control of the concentration of the constituents involved and further experiments involving the concentration used will provide further biological insights.

Example 3

Use of Giant Vesicles to Elucidate the Function of FzlC with FtsZ in Bacterial Cytokinesis and Cell Division in Prokaryotic Organisms.

In most bacteria, the tubulin-like GTPase FtsZ forms an annulus at midcell (the Z-ring) which recruits the division machinery and regulates cell wall remodeling. One poorly understood class of FtsZ regulators mediates its membrane association. Most of what is known about FtsZ's membrane association comes from work in *Escherichia coli*. In that organism, inactivation of both of the known membrane anchors, FtsA and ZipA, destabilizes preformed Z-rings and blocks de novo Z-ring assembly. In vivo and in vitro characterization of the FtsZ-binding protein FzlC suggests that it is one such candidate membrane tether.

Figure 2A:
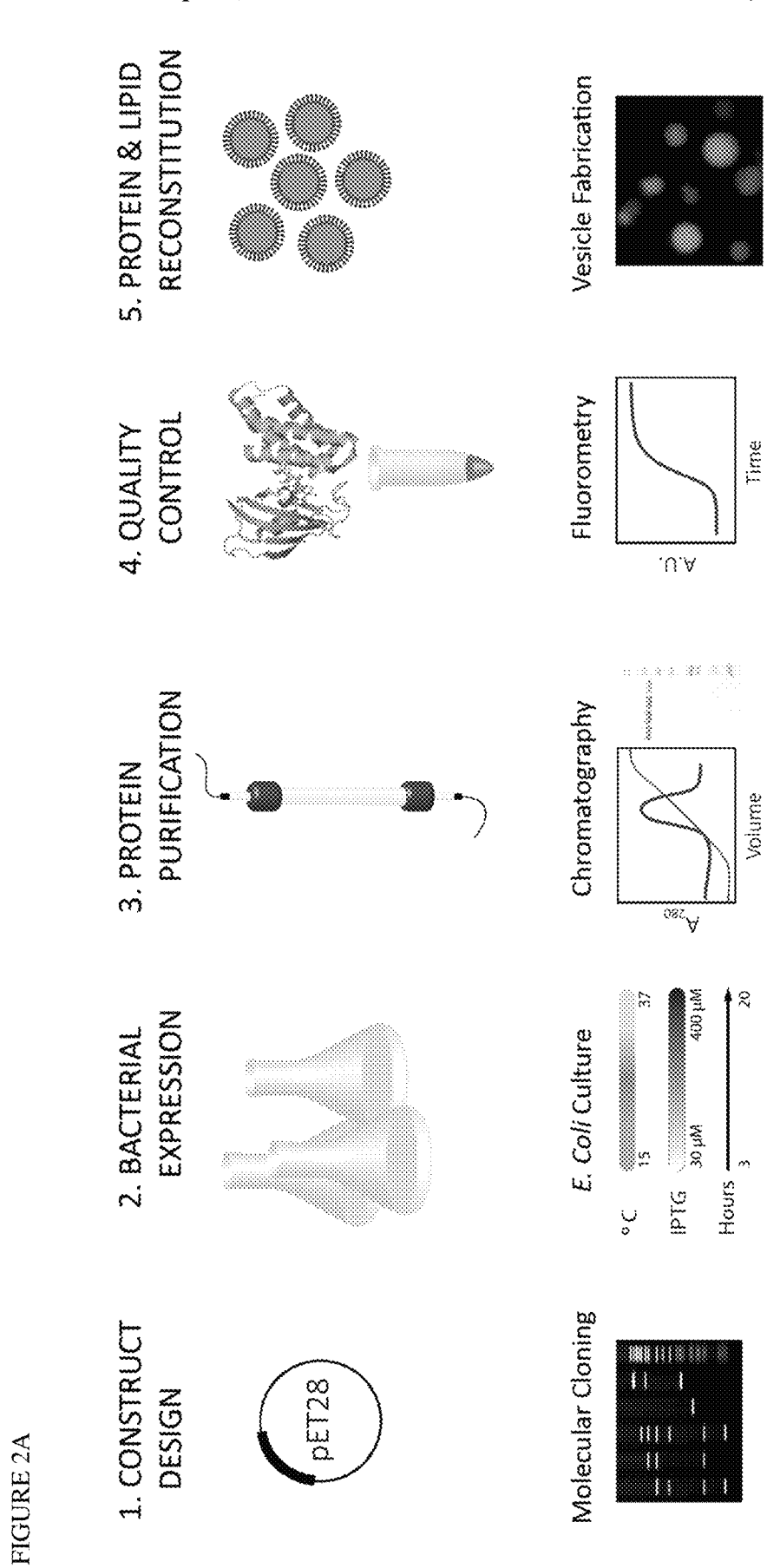
FIGS. 2A-2B. Schematic of the workflow for obtaining the luminal protein material and depiction of the steps involved in assembling the unilamellar vesicles. 2A) Schematic of the workflow to encapsulate functional protein components in the giant unilamellar vesicles. 1) Subcloning the gene of interest in a vector for bacterial expression, 2) optimizing the protein expression condition, 3) isolation of the protein of interest from the endogenous bacterial protein content, 4) assaying for the functionality of the purified protein, and finally 5) the reconstitution of the protein of interest in the vesicles constitute the chore steps for entrapment of functional protein/peptide material in the mimetic cells. 2B) Simplified schematic of the overview of the steps involved in giant vesicle fabrication. This process requires 1) making an emulsion that consists of the luminal content and the inner leaflet lipid material, 2) passing through the emulsion phase over the outer leaflet lipids that are assembled as a monolayer on a disaccharide solution of choice, and finally 3) harvesting the vesicles from the bottom of the tube.
Figure 2B:
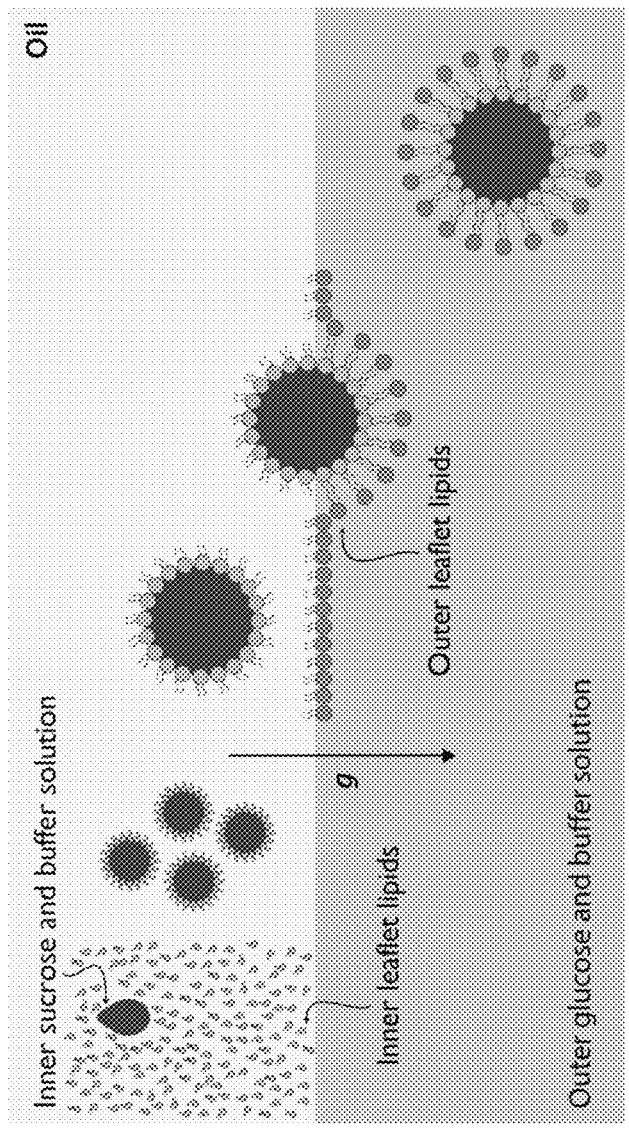

Since FzlC binds both to FtsZ filaments and membranes in vitro, it was hypothesized that FzlC could function as a membrane anchor for FtsZ. The precedence of encapsulating bacterial proteins, including FtsZ membrane tethers, inside giant unilamellar vesicles (GUVs) inspired us to employ the present invention for assaying FtsZ recruitment to membranes by FzlC. The inverted emulsion method was used to encapsulate YFP-FzlC and/or FtsZ-CFP 1/−GTP inside GUVs with outer leaflets composed of 4:1 PC:phosphatidylserine (PS) and inner leaflets composed of 1:1 PG:PC. YFP-FzlC alone localized robustly to the membrane while FtsZ-CFP alone remained luminal under polymerizing (+GTP) and non-polymerizing (−GTP) conditions (FIG. 4A). When we combined YFP-FzlC and FtsZ-CFP+/−GTP, YFP-FzlC invariably localized to the membrane and it recruited FtsZ-CFP to the membrane in a GTP-dependent manner (FIG. 2B). Since FtsZ was recruited to the membrane only in the presence of FzlC and GTP, it was concluded that FzlC can act as a membrane anchor for FtsZ polymers in vitro. We did not observe Z-ring assembly or FtsZ-dependent membrane deformation as reported for *E. coli* FtsZ-YFP-MTS or FtsZ and FtsA encapsulated inside liposomes. However, GUVs containing FzlC and FtsZ polymers were less stable than any of our other GUV preparations and we occasionally observed vesicle shrinkage under these conditions.

Since many FtsZ-binding proteins regulate the localization or activity of FtsZ by altering its superstructure or assembly dynamics, we assessed whether FzlC affected FtsZ polymer structure and/or GTPase activity. At equimolar concentrations of purified proteins, FzlC did not have any obvious effect on FtsZ filament organization, as visualized using negative stain transmission electron microscopy (data not shown). Although filament architecture was not appreciably affected, additional densities were observed along FtsZ filaments in the presence of FzlC, likely reflecting FzlC bound to filaments. The GTPase activity of FtsZ was also unaffected in the presence of FzlC, even when FzlC was added in molar excess (data not shown). These data indicate that the primary biochemical activity of FzlC towards FtsZ is to serve as a membrane anchor.

Example 4

Application of GUVs in Reconstituting Cellular Function: Asymmetric Membrane Deformation.

Figure 6:
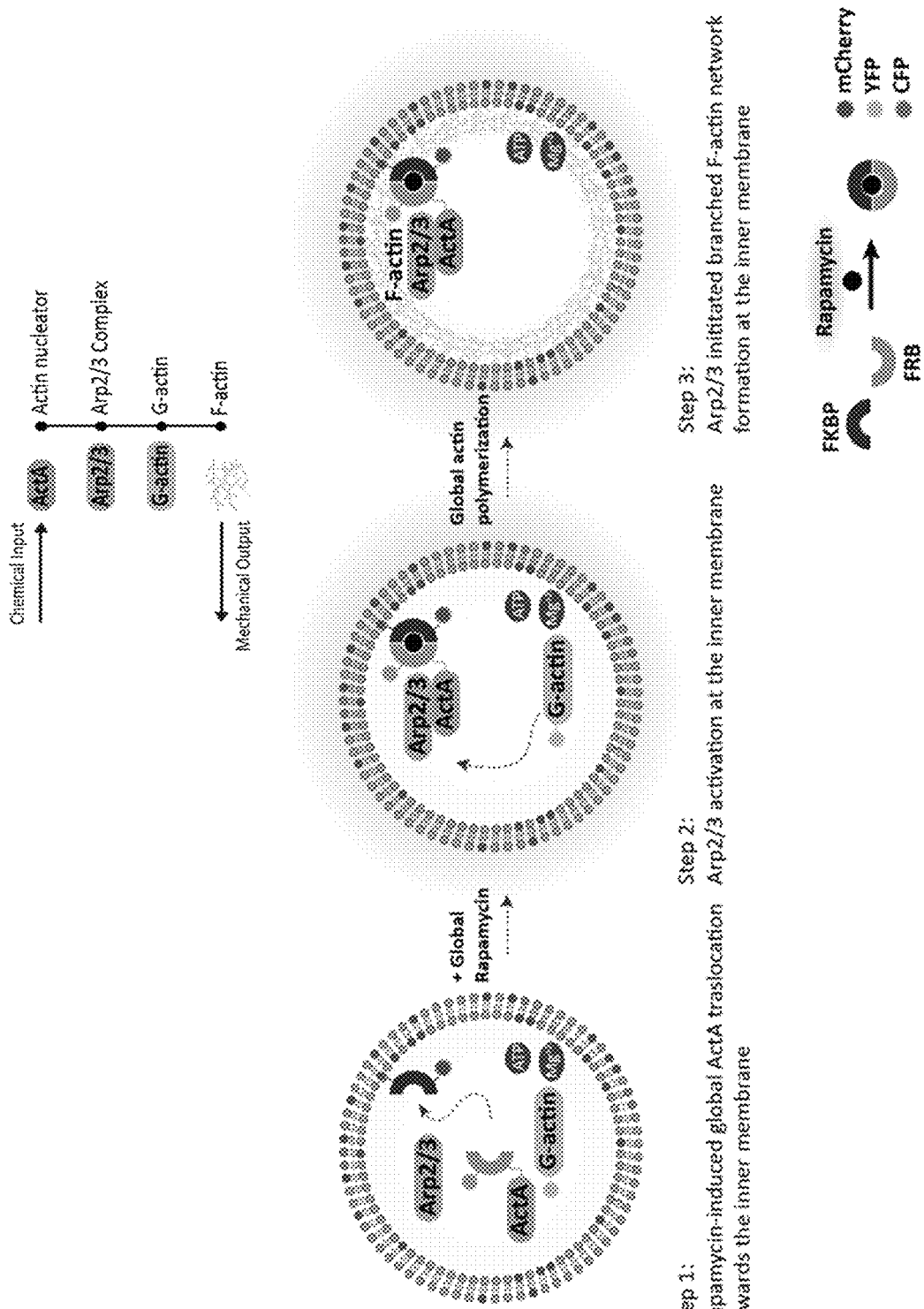
FIG. 6. Schematic diagram of another embodiment of the present invention. The inventors reconstituted minimal actin polymerization machinery inside a GUV. The cellular machinery in the GUV comprises the actin assembly-inducing protein (ActA), the Arp2/3 complex (a seven-subunit protein complex that plays a major role in the regulation of the actin cytoskeleton. It is a major component of the actin cytoskeleton and is found in most actin cytoskeleton-containing eukaryotic cells. Two of its subunits, the Actin-Related Proteins ARP2 and ARP3 closely resemble the structure of monomeric actin and serve as nucleation sites for new actin filaments), globular actin (G-actin), ATP, and $Mg^{2+}$ and is coupled to a FKBP/FRB actuation module. Administration of about 100 μM rapamycin externally triggered actin polymerization on demand through recruitment of ActA from the lumen to the membrane, at a great enough concentration for Arp2/3 activation and the resulting downstream membrane deformation events.

As shown in the schematic diagram in FIG. 6, by reconstituting the minimal actin polymerization machinery (ActA, Arp2/3, G-actin, ATP, and $Mg^{2+}$), inside the GUVs and coupling the upstream ActA to the FKBP/FRB actuation module, it was possible to externally trigger actin polymerization on demand. This was achieved administering rapamycin on the outside of GUVs, which then mediated recruitment of ActA from the lumen to the membrane, thus increasing its concentration in the membrane space to levels high enough for Arp2/3 activation and triggering of the downstream actin polymerization events.

GUV fabrication (Symmetric GUV lipid—POPC:Ni-DGS:PEG2000 94:5:1 (mol:mol:mol) with actin polymerization mixture inside (FIG. 6)

POPC:Ni-DGS:PEG2000 94:5:1 (mol:mol:mol) in chloroform were aliquoted in a vial to the final of 5 mg total lipid content. The vial was dried under vacuum overnight. 4.5 ml of hexadecane and 0.5 ml of silicon oil were added to each vial and the mixture was placed in the oven at a 65° C., gently rotating for 3-4 hours. Right before fabrication of the GUVs the lipids were taken out of the oven and cooled to room temperature for a few minutes to less than 1 hour (this is crucial since if the lipids are at room temperature for over an hour they gradually start dropping out of the solution). The GUVs are made as detailed in the "Example" section. 250 µl of buffered 425 mM glucose solution is pipetted in an Eppendorf tube. 250 µl of the solubilized lipid mixture is gently pipetted on top. The luminal content mixture is prepared in the order, volumes, and concentrations details in Table 1. Next, 250 µl of the solubilized lipids mixture is added to the emulsion mixtures and forcefully flicked to get a turbid emulsion phase. About 220 µl (around 1/4-1/2 of the volume) of the emulsion is gently pipetted on top of the stabilized glucose/lipid bilayers in the Eppendorf tube. Quickly after, the tube is centrifuged at 2,500 g for 2 min. The GUVs are harvested by poking a hole in the bottom of the tube.

Figure 7:
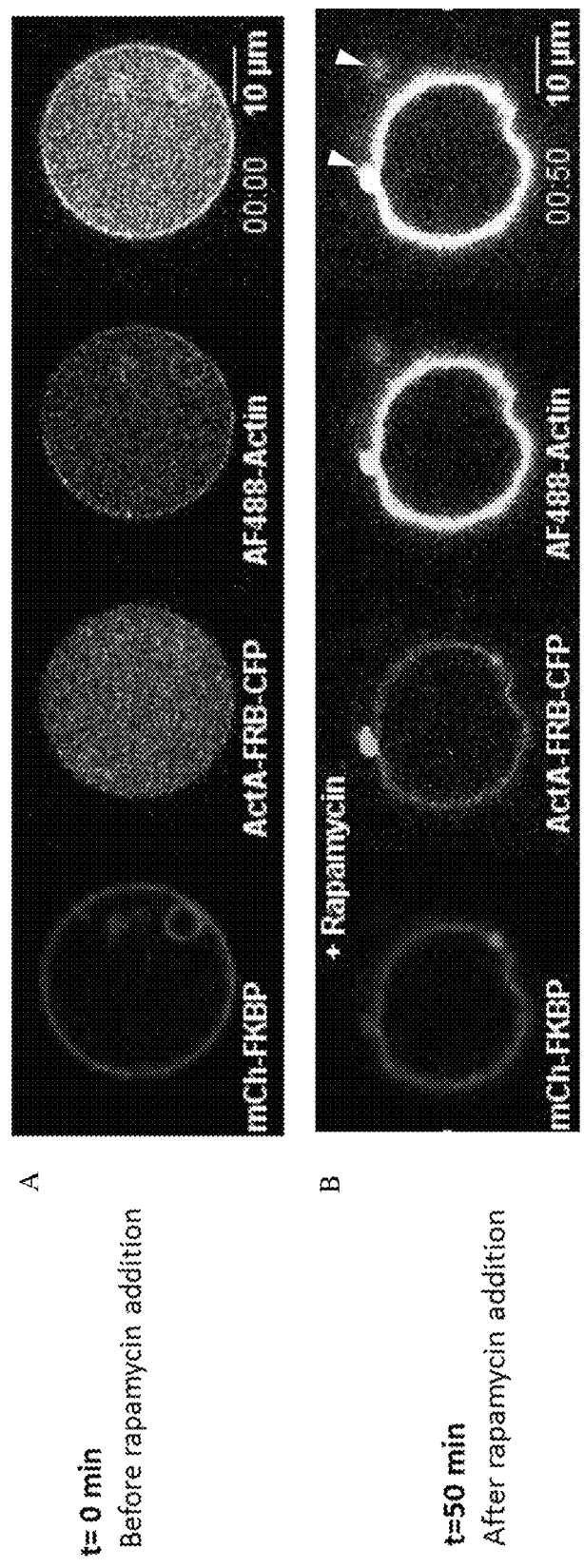
FIG. 7. Actin polymerization inside artificial cells (GUVs) leads to deformation. The addition of rapamycin to the external GUV solution, causes ActA to fuse with the FRB-CFP module, and then the fused components translocate towards the GUV membrane where the mCh-labeled FKBP is present. The ensuing ActA enrichment at the inner membrane activates the Arp2/3 complex, driving the actin polymerization at the inner leaflet (observed by the yellow alexa fluor 488 signal). This Arp2/3 regulated event results in formation of branched actin networks at the membrane, leading to force-imbalance and the eventual mechanical deformation of the GUV membrane (bottom rows), indicated by deformed overall shape of GUV changing from the original perfect sphere shape (top rows).

About 100 µl of the harvested GUVs are placed in an 8-well plate. The GUVs are imaged with a spinning disc confocal microscope (FIG. 7A).

Approximately about 10-15 minutes after imaging the GUVs' basal state, rapamycin is administered. To prepare the rapamycin solution, 10 mM rapamycin stock solubilized in DMSO is mixed with the outer GUV buffer to make a 1 mM rapamycin stock. 11 µl of this 1 mM rapamycin solution is added to the well containing 100 µl of GUVs (final rapamycin concentration is approximately 100 µM).

TABLE 1

Inner GUV Reaction Mixture

| | | | Final Conc. |
|---|---|---|---|
| Sucrose [1M] | 1M | 8.5 µl | 425 mM |
| 5xKin buffer | — | 4 µl | 1x |

TABLE 1-continued

Inner GUV Reaction Mixture

| | | | Final Conc. |
|---|---|---|---|
| ATP | 20 mM | 1 µl | 1 mM |
| mCh-FKBP | 380 µM | 0.5 µl | 9.5 µM |
| 2xstrep-mActA(1-184)-FRB-CFP | 88 µM | 2 µl | 8.8 µM |
| Arp2/3 | 1.5 µM | 2 µl | 0.15 µM |
| G-actin:AF488actin (3:1) | 7.86 µM | 2.5 µl | 0.98 µM |
| Total | | 20 µl | |

By adding rapamycin to the outer GUV solution, ActA fused with the FRB-CFP module translocates towards the membrane where the mCh-labeled FKBP is present. The ensuing ActA enrichment at the inner membrane activates Arp2/3 complex, driving the actin polymerization at the inner leaflet (observed by the yellow alexa fluor 488 signal) (FIG. 7B). This Arp2/3 regulated event results in formation of branched actin networks at the membrane, leading to force-imbalance and the eventual deformation of the GUV membrane (FIG. 7B), indicated by deformed overall shape of GUV changing from the original perfect sphere shape (FIG. 7A).

Figure 8:
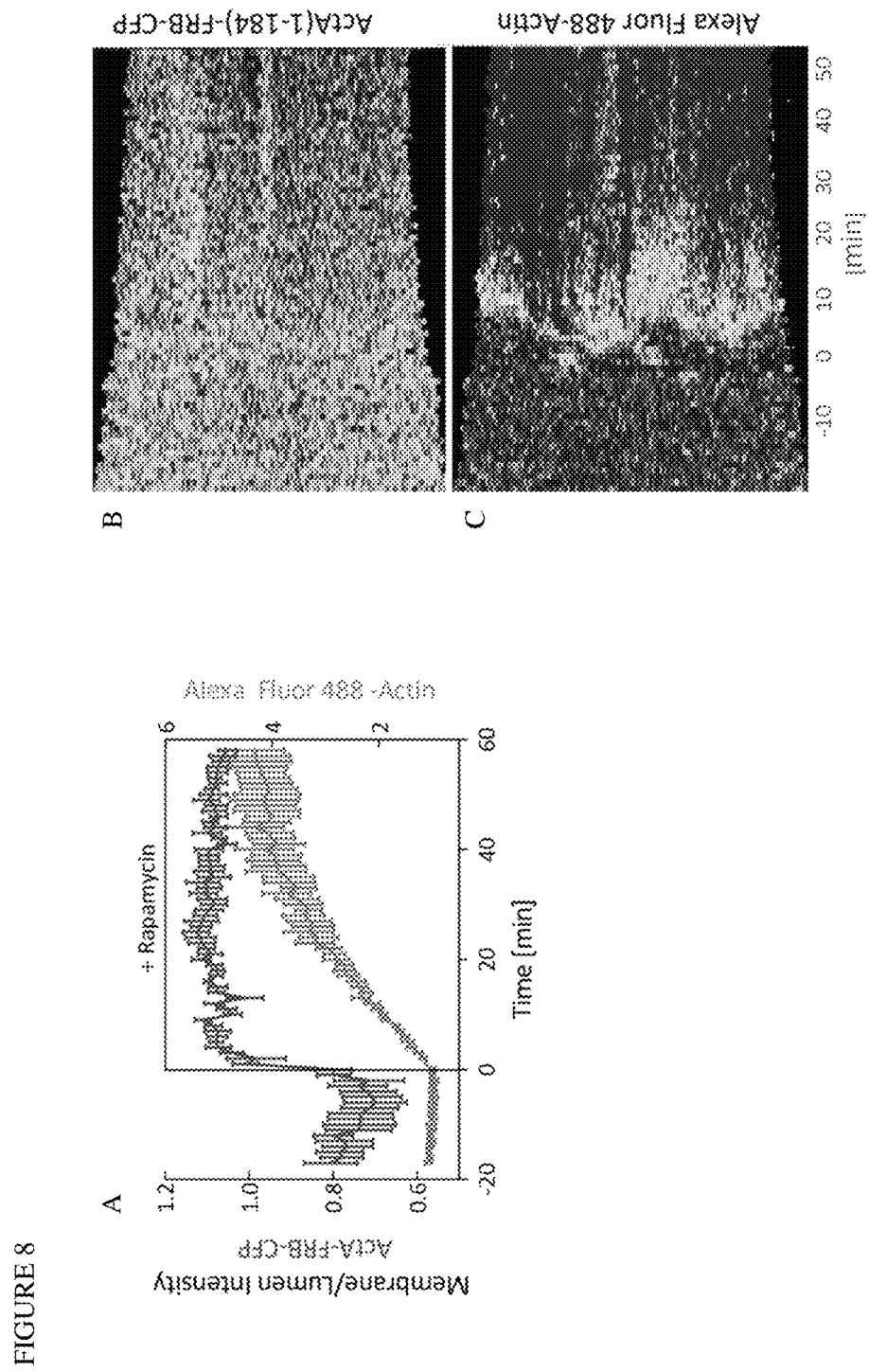
FIG. 8. At left is a graph depicting membrane and lumen intensity of the ActA-FRB-CFP complex and the Alexa fluor 488-Actin in the GUV. At right is a kymograph of the membrane signal intensity for the same two molecules. The rapamycin-induced translocation of actin at the membrane lags behind that of ActA, which is expected given actin's placement as a downstream signaling molecule. This is both evident in the dynamics of ActA and actin translocation towards the membrane (left) and the kymograph of the membrane signal intensity (right) for these two signaling molecules.

The rapamycin-induced translocation of actin at the membrane lags behind that of ActA, which is expected given actin's placement as a downstream signaling molecule. This is both evident in the dynamics of ActA and actin translocation towards the membrane (FIG. 8A) and the kymograph of the membrane signal intensity (FIGS. 8B and 8C) for these two signaling molecules. These kymographs depict the evolution of the Act (FIG. 8B) and actin (FIG. 8C) signal intensity at the membrane as a function of time. The membrane boundary was defined as the membrane area in which the mCh-FKBP membrane marker is present. Using this information, a MATLAB® script was used to create a mask that hides all pixels but the membrane region ones. This mask was applied to the CFP and AF488 channels to calculate the ActA and actin membrane signal intensity and the corresponding kymograph for each frame. The plots in FIG. 8A are generated by dividing the membrane signal to that of the lumen to account for photo-bleaching of the fluorophores. The zero time point marks the rapamycin addition frame.

This deformation embodiment is shown to be capable of being designed to actuate useful processes such as release of therapeutic drugs contained inside GUVs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A giant unilamellar vesicle (GUV) comprising a unilamellar lipid bilayer, wherein the unilamellar lipid bilayer includes the outer surface of the GUV and encloses the inner lumen of the GUV;

wherein the unilamellar lipid bilayer comprises at least a first lipid and second lipid selected from a phosphatidylcholine (PC), phosphatidylserine (PS), phosphatidylglycerol (PG), phosphatidylinositol 4,5-biphosphate (PIP2), and DGS-NTA (Ni), and combinations thereof wherein the first and second lipid and combinations thereof may be the same or different;

and wherein the GUV comprises a chemically inducible dimerization protein in the inner lumen and a binding partner protein on the outer surface; wherein the binding partner protein on the outer surface is fused with myristoylated alanine-rich protein kinase C substrate (MARCKS) or a C2 domain of lactadherin (lact-C2).

2. The GUV of claim 1, wherein the inner lumen comprises a lipid selected from phosphatidylserine (PS), phosphatidylinositol 4,5-biphosphate (PIP2), and phosphatidylglycerol (PG): phosphatidylcholine (PC).

3. The GUV of claim 1, wherein the outer surface comprises a lipid selected from phosphatidylcholine (PC), phosphatidylcholine (PC):phosphatidylserine (PS), and combinations thereof.

4. The GUV of claim 1, wherein the diameter of the GUV is about 1 nm to about 1000 μm.

5. The GUV of claim 1, wherein the first lipid and second lipid of the unilamellar lipid bilayer further comprises PEG2000.

* * * * *